United States Patent
Morishima

(10) Patent No.: US 11,931,007 B2
(45) Date of Patent: Mar. 19, 2024

(54) ENDOSCOPE SYSTEM AND PROPULSION METHOD FOR INSERTION SECTION

(71) Applicant: OLYMPUS CORPORATION, Tokyo (JP)

(72) Inventor: Tetsuya Morishima, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 659 days.

(21) Appl. No.: 17/119,020

(22) Filed: Dec. 11, 2020

(65) Prior Publication Data

US 2021/0093224 A1 Apr. 1, 2021

Related U.S. Application Data

(63) Continuation of application No. PCT/JP2018/022736, filed on Jun. 14, 2018.

(51) Int. Cl.
| | | |
|---|---|---|
| *A61B 1/005* | (2006.01) | |
| *A61B 1/00* | (2006.01) | |
| *A61B 1/05* | (2006.01) | |
| *A61B 1/31* | (2006.01) | |

(Continued)

(52) U.S. Cl.
CPC .......... *A61B 1/0057* (2013.01); *A61B 1/0002* (2013.01); *A61B 1/009* (2022.02); *A61B 1/05* (2013.01); *A61B 1/31* (2013.01); *A61B 5/062* (2013.01); *A61B 34/20* (2016.02); *A61B 1/00009* (2013.01); *A61B 2034/2061* (2016.02)

(58) Field of Classification Search
CPC ... A61B 1/009; A61B 1/31; A61B 2034/2061; A61B 34/20
See application file for complete search history.

(56) References Cited

U.S. PATENT DOCUMENTS

| | | |
|---|---|---|
| 8,641,602 B2 | 2/2014 | Belson |
| 2013/0109919 A1 | 5/2013 | Sugiyama et al. |
| 2017/0042412 A1 | 2/2017 | Takemoto et al. |

FOREIGN PATENT DOCUMENTS

| | | |
|---|---|---|
| EP | 2 583 616 A1 | 4/2013 |
| EP | 3 158 911 A1 | 4/2017 |
| JP | 06-133923 A | 5/1994 |

(Continued)

OTHER PUBLICATIONS

International Search Rpeort dated Aug. 28, 2018 received in PCT/JP2018/022736.

*Primary Examiner* — Amelie R Davis
(74) *Attorney, Agent, or Firm* — Scully, Scott, Murphy & Presser, P.C.

(57) ABSTRACT

An endoscope system includes an insertion section, a first active bending section, a second active bending section, a position-information acquiring section, a first control section, a second control section, and a third control section. The first control section controls, based on a detection result of the position-information acquiring section, a first driving section of the first active bending section such that a first end portion of a first tubular section of the first active bending section moves away from a center point. The first control section controls a second driving section of the second active bending section such that a second end portion of a second tubular section of the second active bending section approaches the center point. The third control section controls the first driving section such that force in a direction of bending the first tubular section in a first bending operation acts on the first end portion.

11 Claims, 17 Drawing Sheets

(51) Int. Cl.
*A61B 5/06* (2006.01)
*A61B 34/20* (2016.01)

(56) References Cited

FOREIGN PATENT DOCUMENTS

| | | |
|---|---|---|
| JP | 06-154154 A | 6/1994 |
| JP | 2008-253774 A | 10/2008 |
| JP | 2009-195321 A | 9/2009 |
| JP | 2013-027466 A | 2/2013 |
| WO | 2012132637 A | 10/2012 |
| WO | 2015/194317 A1 | 12/2015 |
| WO | 2017014308 A1 | 1/2017 |

ENDOSCOPE SYSTEM AND PROPULSION METHOD FOR INSERTION SECTION

CROSS REFERENCE TO RELATED APPLICATION

This application is a continuation application of PCT/JP2018/022736 filed on Jun. 14, 2018, the entire contents of which are incorporated herein by this reference.

BACKGROUND OF THE INVENTION

1. Field of the Invention

The present invention relates to an endoscope system that propels a distal end of an insertion section and a propulsion method for the insertion section.

2. Description of the Related Art

In recent years, an endoscope apparatus including an elongated insertion section has been used in a medical field and an industrial field. In the medical field, the endoscope apparatus is widely used for observation of organs, therapeutic measures performed using a treatment instrument, a surgical operation under endoscopic observation, and the like.

In the endoscope apparatus used in the medical field, a bending section is provided on a distal end side of the insertion section in order to facilitate insertion into a bending lumen such as a large intestine. For example, when the endoscope apparatus is used for an inspection of the large intestine, a surgeon inserts, toward a depth of the large intestine, the distal end of the insertion section inserted into the large intestine from an anus. In a sigmoid colon present in a position near the anus, a flexible tube section of the insertion section is deformed according to a bending shape of the sigmoid colon. When the distal end of the insertion section reaches a combining part of the sigmoid colon and a descending colon, the surgeon bends the bending section and inserts the distal end of the insertion section into the descending colon.

Incidentally, in a state in which the distal end of the insertion section is inserted slightly further on the descending colon side than the combining part of the sigmoid colon and the descending colon, when the insertion section is further pushed in, the insertion section pushes an intestinal wall of the sigmoid colon. Accordingly, in this state, operation for pushing in the insertion section is less easily transmitted to the distal end side. In order to prevent the insertion section from further pushing the intestinal wall of the sigmoid colon, it is desirable to advance the distal end of the insertion section to the depth side without pushing in the insertion section.

The specification of U.S. Pat. No. 8,641,602 B2 discloses an endoscope in which respective sections of an endoscope main body are individually controlled by an actuator, whereby, when the endoscope main body is advanced or retracted, a curved line is propagated to be fixed in a space.

Japanese Patent Application Laid-Open Publication No. 2009-195321 discloses an endoscope apparatus in which, in a state in which a balloon provided in an insertion section is fixed to an intestinal wall of a sigmoid colon, the insertion section is extended and a distal end of the insertion section is advanced from a combining part of the sigmoid colon and a descending colon toward a depth.

SUMMARY OF THE INVENTION

An endoscope system according to an aspect of the present invention includes: an insertion section including a distal end and a proximal end located at both ends in a longitudinal direction, the insertion section being inserted, from an inlet of a lumen of a subject toward a depth, into the lumen from the distal end side; a first active bending section provided in the insertion section and including a first tubular section having flexibility and including a first end portion located on the distal end side, and a first driving section that bends the first tubular section; a second active bending section provided further on the distal end side than the first tubular section in the insertion section and including a second tubular section having flexibility and including a second end portion located on the distal end side, and a second driving section that bends the second tubular section; and a processor. The processor acquires information indicating whether the distal end is located further on a side of the depth than a center point located in a center in the longitudinal direction in a center axis of a predetermined curve part in the lumen, when acquiring information indicating that the distal end is located further on the side of the depth than the center point, controls the first driving section such that a first bending operation in which the first end portion moves away from a center point of an imaginary circle including an arc obtained by approximating the center axis or an imaginary ellipse including an elliptical arc obtained by approximating the center axis is executed, controls the second driving section such that, after the execution of the first bending operation, a second bending operation in which the second end portion approaches the center point is executed, and controls the first driving section such that, during the execution of the second bending operation, operation in which a force in a direction of bending the first tubular section in the first bending operation acts on the first end portion is executed.

A propulsion method for an insertion section according to an aspect of the present invention is a propulsion method for an insertion section in an endoscope system including an insertion section including a distal end and a proximal end located at both ends in a longitudinal direction, the insertion section being inserted, from an inlet of a lumen of a subject toward a depth, into the lumen from the distal end side, a first active bending section provided in the insertion section and including a first tubular section having flexibility and including a first end portion located on the distal end side, and a second active bending section provided further on the distal end side than the first tubular section in the insertion section and including a second tubular section having flexibility and including a second end portion located on the distal end side, the propulsion method including: causing the first active bending section to operate such that, when the distal end is located further on a side of the depth than a center point located in a center in the longitudinal direction in a center axis of a predetermined curve part in the lumen, a first bending operation in which the first end portion moves away from a center point of an imaginary circle including an arc obtained by approximating the center axis or an imaginary ellipse including an elliptical arc obtained by approximating the center axis is executed; causing the second active bending section to operate such that, after the execution of the first bending operation, a second bending operation in which the second end portion approaches the center point is executed; and causing the first active bending section to operate such that, during the execution of the second bending operation, operation in which a force in a direction of bending the first tubular section in the first bending operation acts on the first end portion is executed.

BRIEF DESCRIPTION OF THE DRAWINGS

FIG. 10 is an explanatory diagram showing a step following the step shown in

FIG. 9;

DETAILED DESCRIPTION OF THE PREFERRED EMBODIMENTS

Embodiments of the present invention are explained below with reference to the drawings.

First Embodiment (Configuration of an Endoscope System)

Figure 1:
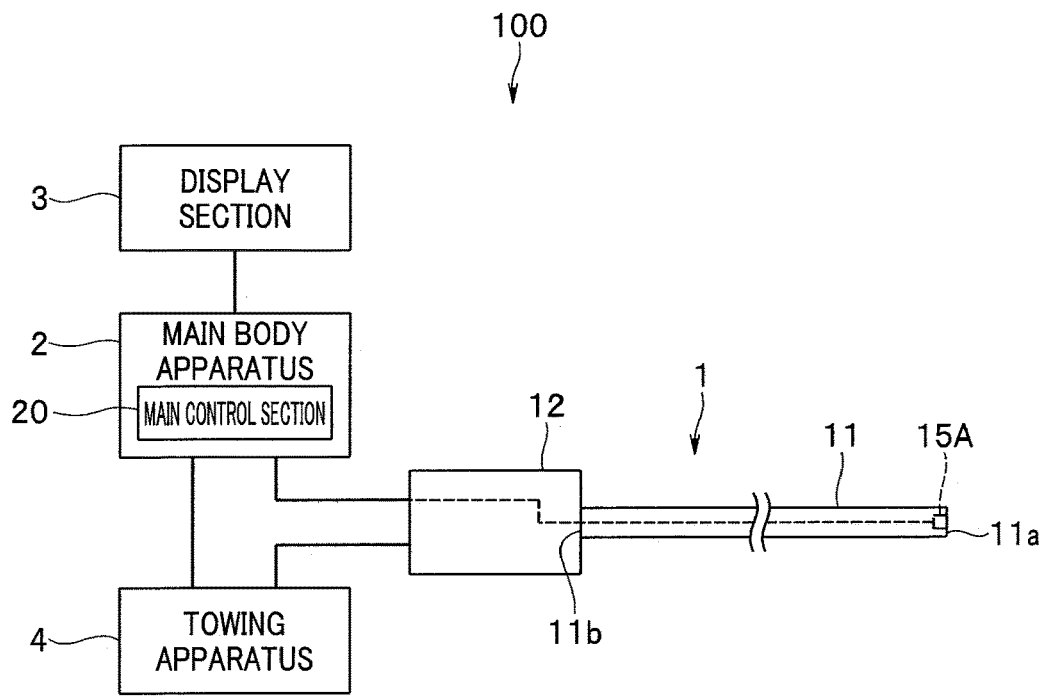
FIG. 1 is an explanatory diagram showing a schematic configuration of an endoscope system according to a first embodiment of the present invention.
Figure 2:
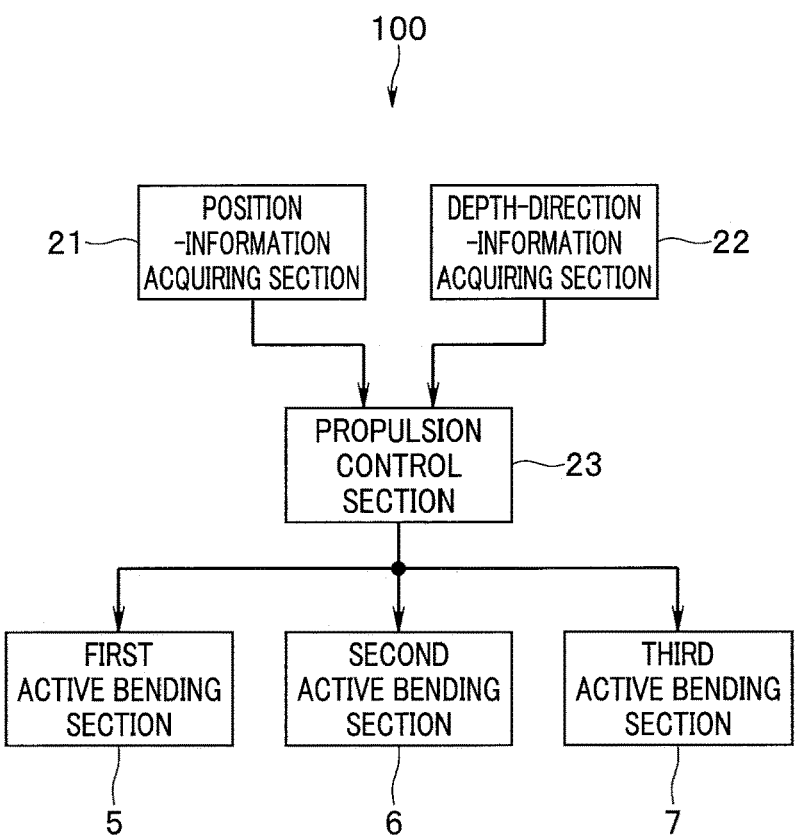
FIG. 2 is a functional block diagram showing a configuration of the endoscope system according to the first embodiment of the present invention.

First, an endoscope system according to a first embodiment of the present invention is explained. An endoscope system 100 according to the present embodiment is a medical endoscope system. A schematic configuration of the endoscope system 100 is explained with reference to FIG. 1 and FIG. 2. FIG. 1 is an explanatory diagram showing the schematic configuration of the endoscope system 100. FIG. 2 is a functional block diagram showing a configuration of the endoscope system 100.

As shown in FIG. 1, the endoscope system 100 includes an endoscope 1, a main body apparatus 2, a display section 3, and a towing apparatus 4. The endoscope 1 is connected to the main body apparatus 2 and the towing apparatus 4. The display section 3 and the towing apparatus 4 are connected to the main body apparatus 2.

The endoscope 1 includes an insertion section 11 having an elongated shape and an operation section 12. The insertion section 11 includes a distal end 11a and a proximal end 11b located at both ends in a longitudinal direction and is inserted, from an inlet of a lumen of a subject toward a depth, into the lumen from the distal end 11a side. An image pickup device 15A is provided at a distal end portion of the insertion section 11. The image pickup device 15A is configured by, for example, a CCD or a CMOS. The operation section 12 is connected to the proximal end 11b of the insertion section 11.

A not-shown illumination apparatus is connected to the endoscope 1. The illumination apparatus generates illumination light irradiated on an object in the lumen. The illumination light is transmitted by a light guide provided in the endoscope 1 and irradiated on the object from an illumination window provided at the distal end portion of the insertion section 11. The image pickup device 15A photoelectrically converts reflected light of the object and generates an image pickup signal. Note that, instead of providing the illumination apparatus and the light guide, a light emitting element such as an LED may be provided at the distal end portion of the insertion section 11.

The image pickup signal generated by the image pickup device 15A is outputted to the main body apparatus 2. The main body apparatus 2 is configured as a video processor and includes a main control section 20 that controls the endoscope 1 and performs predetermined image processing on the image pickup signal. Examples of the predetermined image processing include image adjustment such as gain adjustment, white balance adjustment, gamma correction, contour emphasis correction, and enlargement and reduction adjustment. The main body apparatus 2 outputs the image pickup signal, on which the predetermined image processing is performed, to the display section 3. The display section 3 is configured by a monitor apparatus or the like and displays an image pickup image outputted from the main body apparatus 2 on a screen.

As shown in FIG. 2, the endoscope system 100 further includes a first active bending section 5, a second active bending section 6, and a third active bending section 7. Each of the first to third active bending sections 5 to 7 includes a tubular section provided in the insertion section 11 of the endoscope 1 and a driving section that bends the tubular section. In the present embodiment, the driving section includes a plurality of wires inserted through the insertion section 11. The towing apparatus 4 shown in FIG. 1 includes a towing section that tows the plurality of wires.

As shown in FIG. 2, the endoscope system 100 further includes a position-information acquiring section 21, a depth-direction-information acquiring section 22, and a propulsion control section 23. The position-information acquiring section 21, the depth-direction-information acquiring section 22, and the propulsion control section 23 are respectively controlled by the main control section 20 shown in FIG. 1.

The position-information acquiring section 21 acquires information having a correspondence relation with a position of the distal end 11a of the insertion section 11 (hereinafter referred to as first position information) and information having a correspondence relation with a position of a tubular section of the second active bending section 6 (hereinafter referred to as second position information) in the lumen. The depth-direction-information acquiring section acquires depth direction information indicating a direction of a depth of the lumen based on the position of the distal end 11a of the insertion section 11. In order to propel the distal end 11a of the insertion section 11 toward the depth of the lumen, the propulsion control section 23 controls a shape of the tubular section of each of the first to third active bending sections 5 to 7 based on the first position information, the second position information, and the depth direction information.

Figure 3:
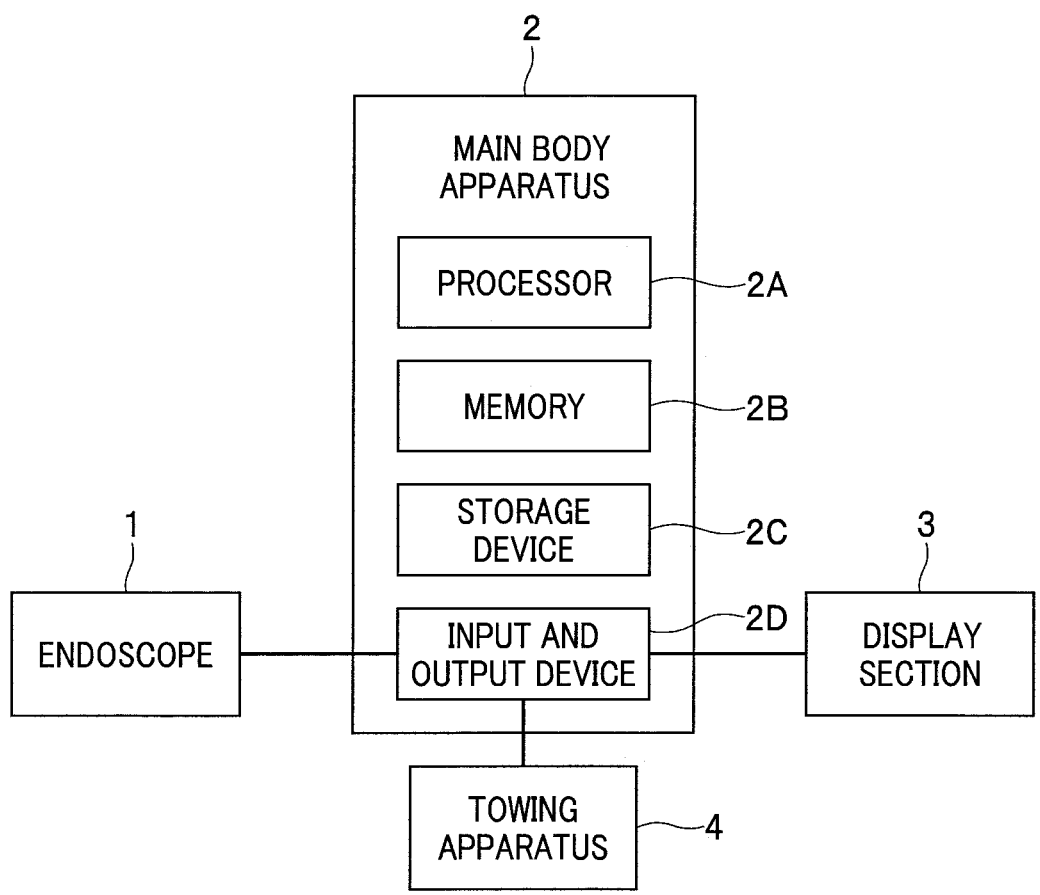
FIG. 3 is an explanatory diagram showing an example of a hardware configuration of a main body apparatus in the first embodiment of the present invention.

A hardware configuration of the main body apparatus 2 is explained with reference to FIG. 3. FIG. 3 is an explanatory diagram showing an example of the hardware configuration of the main body apparatus 2. In the example shown in FIG. 3, the main body apparatus 2 is configured by a processor 2A, a memory 2B, a storage device 2C, and an input and output section 2D.

The processor 2A is used in order to execute at least a part of functions of the main control section 20, the position-information acquiring section 21, the depth-direction-information acquiring section 22, and the propulsion control section 23. The processor 2A is configured by, for example, an FPGA (field programmable gate array). At least a part of the main control section 20, the position-information acquiring section 21, the depth-direction-information acquiring section 22, and the propulsion control section 23 may be configured as a circuit block in the FPGA.

The memory 2B is configured by a rewritable volatile storage element such as a RAM. The storage device 2C is configured by a rewritable nonvolatile storage device such as a flash memory or a magnetic disk device. The input and output section 2D is used to perform transmission and reception of signals between the main body apparatus 2 and an outside.

Note that the processor 2A may be configured by a central processing unit (hereinafter described as CPU). In this case, at least a part of functions of the main control section 20, the position-information acquiring section 21, the depth-direction-information acquiring section 22, and the propulsion control section 23 may be realized by the CPU reading out a program from the storage device 2C or not-shown another storage device and executing the program.

The hardware configuration of the main body apparatus 2 is not limited to the example shown in FIG. 3. For example, each of the main control section 20, the position-information acquiring section 21, the depth-direction-information acquiring section 22, and the propulsion control section 23 may be configured as a separate electronic circuit.

(Configurations of the Active Bending Sections)

Figure 4:
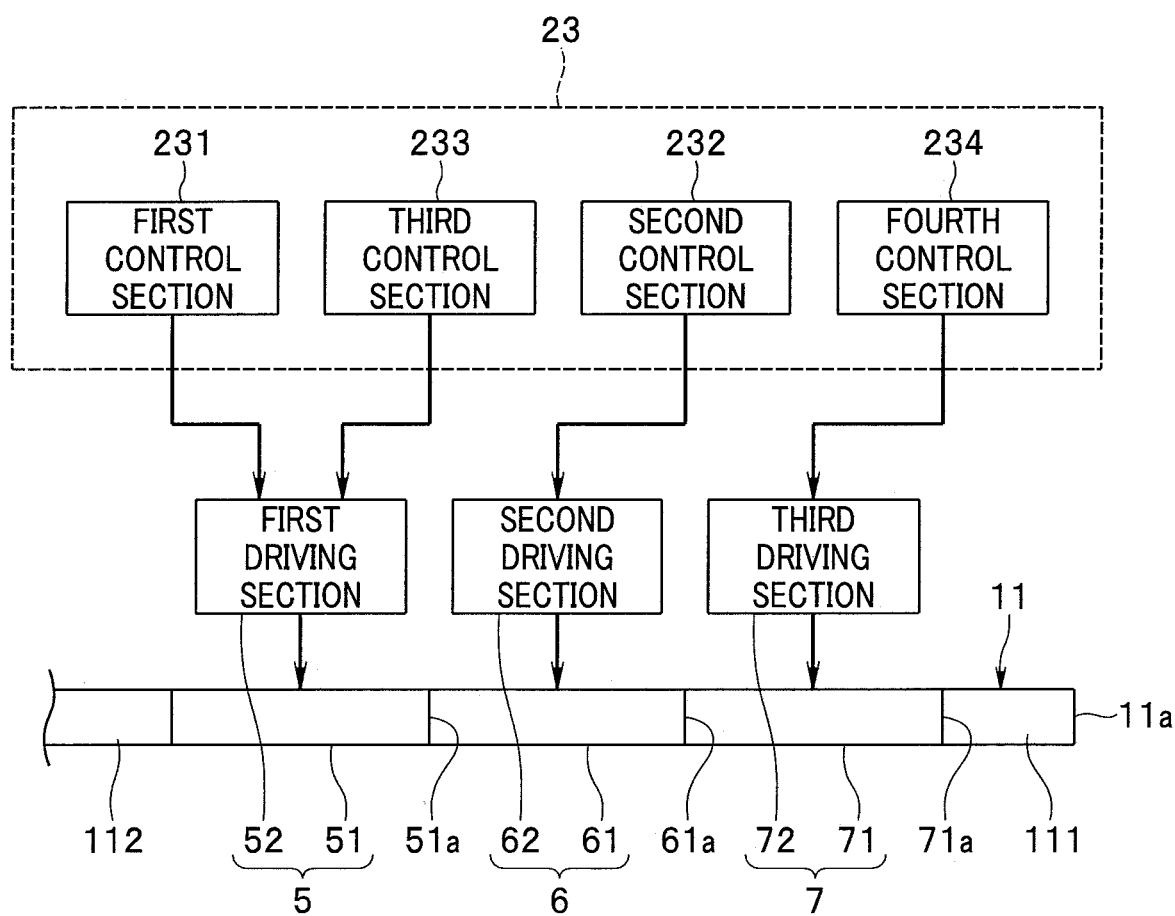
FIG. 4 is a functional block diagram showing configurations of first to third active bending sections and a propulsion control section in the first embodiment of the present invention.

Subsequently, configurations of the first to third active bending sections 5 to 7 are explained with reference to FIG. 4. FIG. 4 is a functional block diagram showing configurations of the first to third active bending sections 5 to 7 and the propulsion control section 23.

The first active bending section 5 includes a first tubular section 51 provided in the insertion section 11 and a first driving section 52 that bends the first tubular section 51. The first tubular section 51 has flexibility and includes a first end portion 51a located on the distal end 11a side of the insertion section 11.

The second active bending section 6 includes a second tubular section 61 provided further on the distal end 11a side than the first tubular section 51 in the insertion section 11 and a second driving section 62 that bends the second tubular section 61. The second tubular section 61 may be coupled to the first end portion 51a of the first tubular section 51 or may be disposed at a predetermined interval from the first tubular section 51. The second tubular section 61 has flexibility and includes a second end portion 61a located on the distal end 11a side of the insertion section 11.

The third active bending section 7 includes a third tubular section 71 provided further on the distal end 11a side than the second tubular section 61 in the insertion section 11 and a third driving section 72 that bends the third tubular section 71. The third tubular section 71 may be coupled to the second end portion 61a of the second tubular section 61 or may be disposed at a predetermined interval from the second tubular section 61. In the latter case, a flexible tube section having flexibility may be provided between the second tubular section 61 and the third tubular section 71. The third tubular section 71 has flexibility and includes a third end portion 71a located on the distal end 11a side of the insertion section 11. The third end portion 71a is present in a position away from the distal end 11a of the insertion section 11.

Note that the insertion section 11 includes a distal end portion 111 provided further on the distal end 11a side than the first tubular section 51 and a flexible tube section 112 provided further on the proximal end 11b side (see FIG. 1) than the first tubular section 51. The distal end portion 111 includes the distal end 11a of the insertion section 11 and is configured by a rigid member. The flexible tube section 112 has flexibility.

Figure 5:
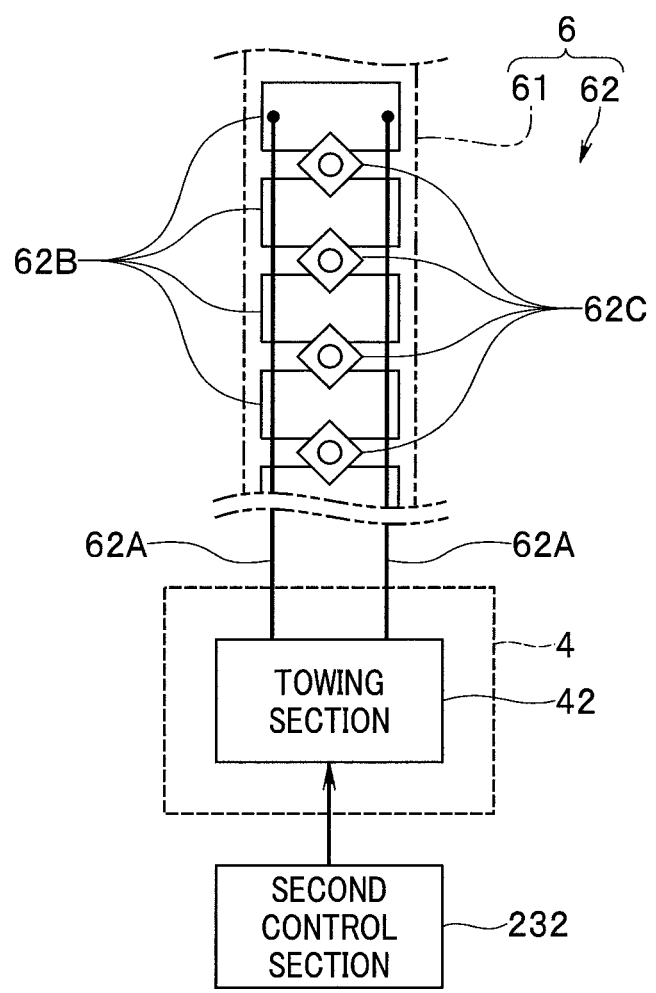
FIG. 5 is an explanatory diagram schematically showing a configuration of a second active bending section in the first embodiment of the present invention.

In the present embodiment, each of the first to third driving sections 52, 62, and 72 includes a plurality of wires inserted through the insertion section 11. A configuration of the second driving section 62 is explained in detail with reference to FIG. 5. In the following explanation, the plurality of wires of the second driving section 62 are represented by a sign 62A. In FIG. 5, two wires 62A among the plurality of wires 62A are shown. The second driving section 62 includes, as the plurality of wires 62A, two or more (four example, four) wires 62A.

The second driving section 62 includes, besides the plurality of wires 62A, a plurality of bending pieces 62B provided in the second tubular section 61. The plurality of bending pieces 62B are coupled in the longitudinal direction of the second tubular section 61. Two bending pieces 62B adjacent to each other are turnably coupled by a coupling member 62C.

The second driving section 62 further includes a towing section 42 provided in the towing apparatus 4. The towing section 42 is configured by a motor for towing each of the plurality of wires 62A. One end portion of each of the plurality of wires 62A is fixed to the bending piece 62B present in a position closest to the distal end 11a in the longitudinal direction of the insertion section 11. The other end portion of each of the plurality of wires 62A is fixed to the motor of the towing section 42.

Figure 6:
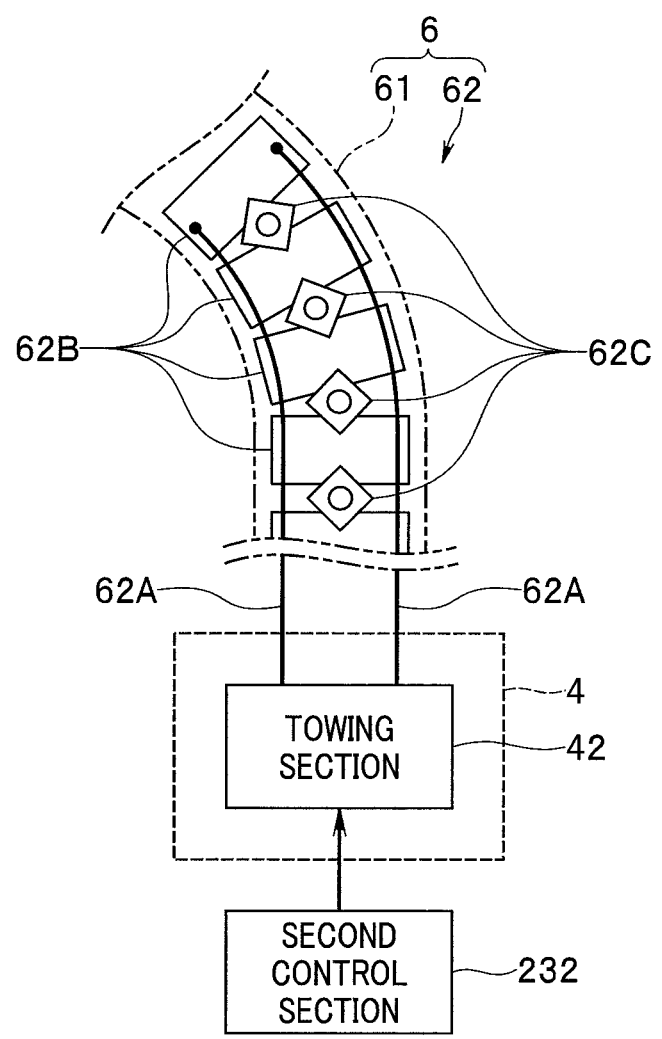
FIG. 6 is an explanatory diagram for explaining operation of a second driving section in the first embodiment of the present invention.

Subsequently, operation of the second driving section 62 is explained with reference to FIG. 6. In the present embodiment, the towing section 42 of the second driving section 62 tows any wire 62A among the plurality of wires 62A, whereby the second tubular section 61 bends. In FIG. 6, an example is shown in which the wire 62A on the left side in FIG. 6 is towed, the wire 62A on the right side in FIG. 6 is slacked, and the second tubular section 61 is bent. A direction and a size of the bending of the second tubular section 61 can be controlled according to a towing amount of each of the plurality of wires 62A.

A configuration and operation of each of the first driving section 52 and the third driving section 72 are the same as the configuration and the operation of the second driving section 62 explained with reference to FIG. 5 and FIG. 6. In other words, the first driving section 52 includes a plurality of wires, a plurality bending pieces provided in the first tubular section 51, and a towing section provided in the towing apparatus 4. In the present embodiment, the towing section of the first driving section 52 tows any wire among the plurality of wires, whereby the first tubular section 51 bends. In the following explanation, the plurality of wires of the first driving section 52 are represented by a sign 52A and the towing section of the first driving section 52 is represented by a sign 41.

The third driving section 72 includes a plurality of wires, a plurality of bending pieces provided in the third tubular section 71, and a towing section provided in the towing apparatus 4. In the present embodiment, the towing section of the third driving section 72 tows any wire among the plurality of wires, whereby the third tubular section 71 bends. In the following explanation, the plurality of wires of the third driving section 72 are represented by a sign 72A and the towing section of the third driving section 72 is represented by a sign 43.

(Configuration of the Propulsion Control Section)

Subsequently, a configuration of the propulsion control section 23 is explained with reference to FIG. 4. The propulsion control section 23 includes a first control section 231, a second control section 232, a third control section 233, and a fourth control section 234. The first control section 231 and the third control section 233 respectively control the first driving section 52. In the present embodiment, the first control section 231 and the third control section 233 respectively control the towing section 41 of the first driving section 52 to thereby control a towing amount of the plurality of wires 52A of the first driving section 52, thereby controlling a shape of the first tubular section 51.

The second control section 232 controls the second driving section 62. In the present embodiment, the second control section 232 controls the towing section 42 of the second driving section 62 to thereby control a towing amount of the plurality of wires 62A of the second driving section 62, thereby controlling a shape of the second tubular section 61.

The fourth control section 234 controls the third driving section 72. In the present embodiment, the fourth control section 234 controls the towing section 43 of the third driving section 72 to thereby control a towing amount of the plurality of wires 72A of the third driving section 72, thereby controlling a shape of the third tubular section 71.

(Configuration of the Position-Information Acquiring Section)

Figure 7:
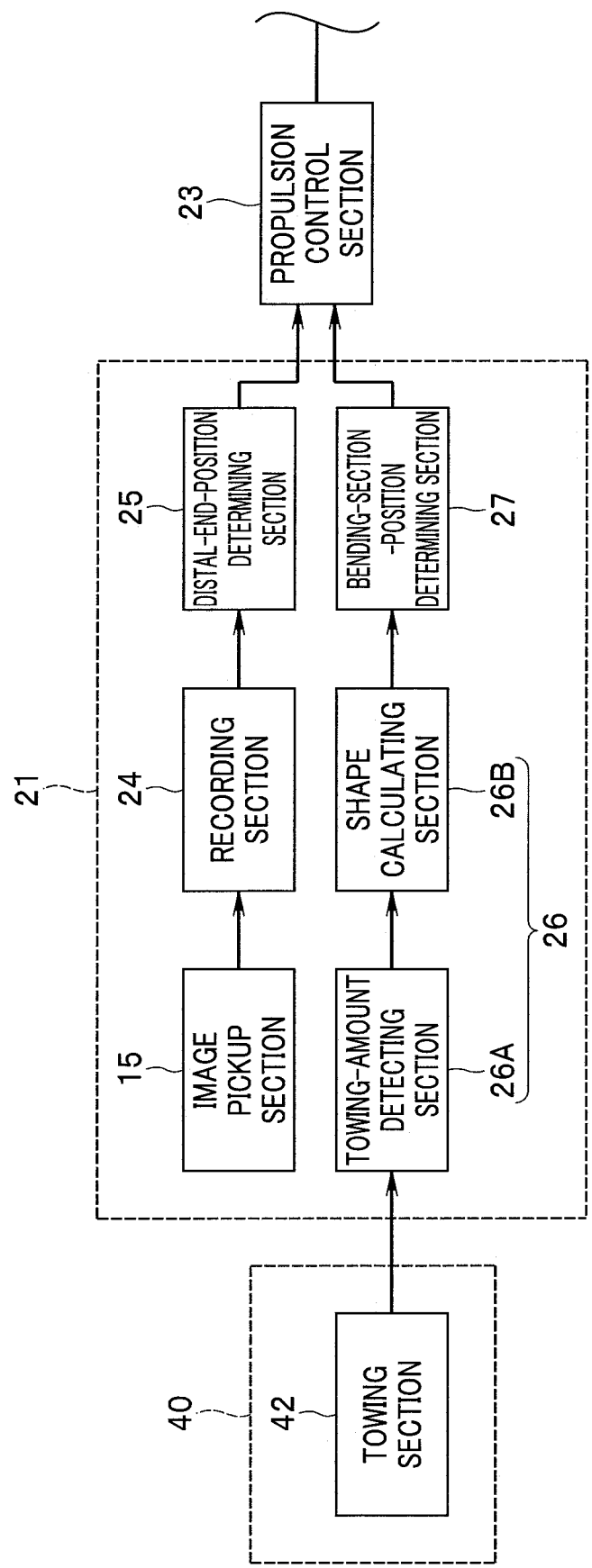
FIG. 7 is a functional block diagram showing a configuration of a position-information acquiring section in the first embodiment of the present invention.

Subsequently, a configuration of the position-information acquiring section 21 is explained with reference to FIG. 7. FIG. 7 is a functional block diagram showing the configuration of the position-information acquiring section 21. In the present embodiment, the position-information acquiring section 21 includes an image pickup section 15, a recording section 24, and a distal-end-position determining section 25. The image pickup section 15 includes the image pickup device 15A (see FIG. 1) and acquires, as an image of an object in a lumen of a subject, an image pickup signal generated by the image pickup device 15A. At least a part of the image pickup section 15 including the image pickup device 15A is provided in the endoscope 1.

The recording section 24 is configured by, for example, at least one of the memory 2B and the storage device 2C shown in FIG. 3 and records an image acquired by the image pickup section 15. Note that the recording section 24 may record, as the image, the image pickup signal generated by the image pickup device 15A or may record, as the image, the image pickup signal on which the predetermined image processing is performed by the main control section 20 of the main body apparatus 2.

The distal-end-position determining section 25 reads out a plurality of images recorded in the recording section 24 and determines, based on a history of changes of the plurality of images, a position of the distal end 11a of the insertion section 11. More specifically, the distal-end-position determining section 25 estimates, with image matching or the like, a position of the distal end 11a of the insertion section 11 from the images and determines a present position of the distal end 11a of the insertion section 11 from a history of changes of the estimated position of the distal end 11a of the insertion section 11.

The position-information acquiring section 21 further includes a shape sensor 26 and a bending-section-position determining section 27. The shape sensor 26 detects a shape of the second tubular section 61 of the second active bending section 6. The bending-section-position determining section 27 determines, based on a detection result of the shape sensor 26, that is, the shape of the second tubular section 61, a position of the second end portion 61a of the second tubular section 61.

In the present embodiment, the shape sensor 26 includes a towing-amount detecting section 26A and a shape calculating section 26B. The towing-amount detecting section 26A detects a towing amount of each of the plurality of wires 62A (see FIG. 5) of the second driving section 62 of the second active bending section 6. The towing amount of the wire 62A is detected by, for example, detecting a rotation angle and the number of rotations of the motor configuring the towing section 42 of the second driving section 62.

The shape calculating section 26B calculates a shape of the second tubular section 61, that is, a direction and a size of bending of the second tubular section 61 and calculates a curvature of the second tubular section 61, based on the towing amount of each of the plurality of wires 62A detected by the towing-amount detecting section 26A.

Note that the shape sensor 26 may be configured to be able to detect a shape of the first tubular section 51 of the first active bending section 5 and a shape of the third tubular section 71 of the third active bending section 7 in addition to the shape of the second tubular section 61 of the second active bending section 6. More specifically, for example, the towing-amount detecting section 26A may detect a towing amount of each of the plurality of wires 52A of the first driving section 52 of the first active bending section 5 and a towing amount of each of the plurality of wires 72A of the third driving section 72 of the third active bending section 7. The shape calculating section 26B may calculate a shape and a curvature of the second tubular section 61 based on the towing amount of each of the plurality of wires 52A and calculates a shape and a curvature of the third tubular section 71 based on the towing amount of each of the plurality of wires 72A.

(Configuration of the Depth-Direction-Information Acquiring Section)

Figure 8:
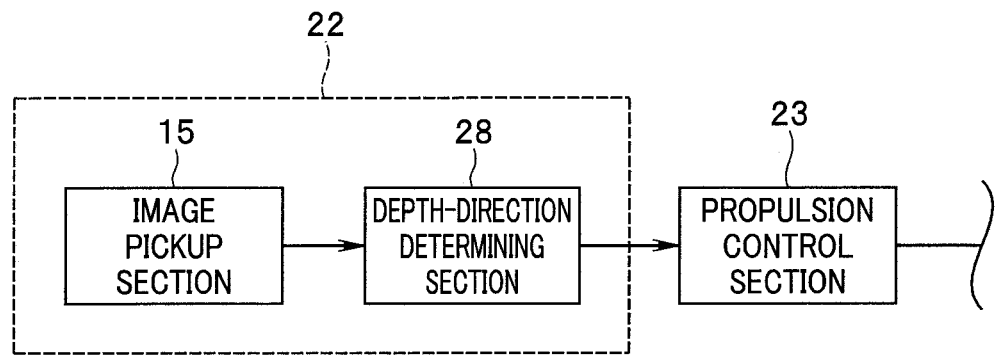
FIG. 8 is a functional block diagram showing a configuration of a depth-direction-information acquiring section in the first embodiment of the present invention.

Subsequently, a configuration of the depth-direction-information acquiring section 22 is explained with reference to FIG. 8. FIG. 8 is a functional block diagram showing the configuration of the depth-direction-information acquiring section 22. In the present embodiment, the depth-direction-information acquiring section 22 includes the image pickup section 15 and a depth-direction determining section 28. Note that, as shown in FIG. 7, the image pickup section 15 is also a component of the position-information acquiring section 21.

The depth-direction-information acquiring section 22 determines, based on an image acquired by the image pickup section 15, a direction of a depth of a lumen based on the position of the distal end 11a of the insertion section 11. More specifically, for example, the depth-direction-information acquiring section 22 estimates a direction of the distal end 11a of the insertion section 11 by analyzing the image and determines a direction of the depth of the lumen based on the estimated direction of the distal end 11a of the insertion section 11.

(First Example of a Propulsion Operation)

Subsequently, a propulsion operation for the insertion section 11 in the present embodiment is explained. A case in which a lumen of a subject is an intestinal tract of a large intestine is explained as an example.

First, a first example of the propulsion operation for the insertion section 11 is explained with reference to FIG. 9 to FIG. 12. The first example is an example in which the distal end 11a of the insertion section 11 is propelled in a portion near a curve part formed in a combining part of a sigmoid colon and a descending colon.

Figure 9:
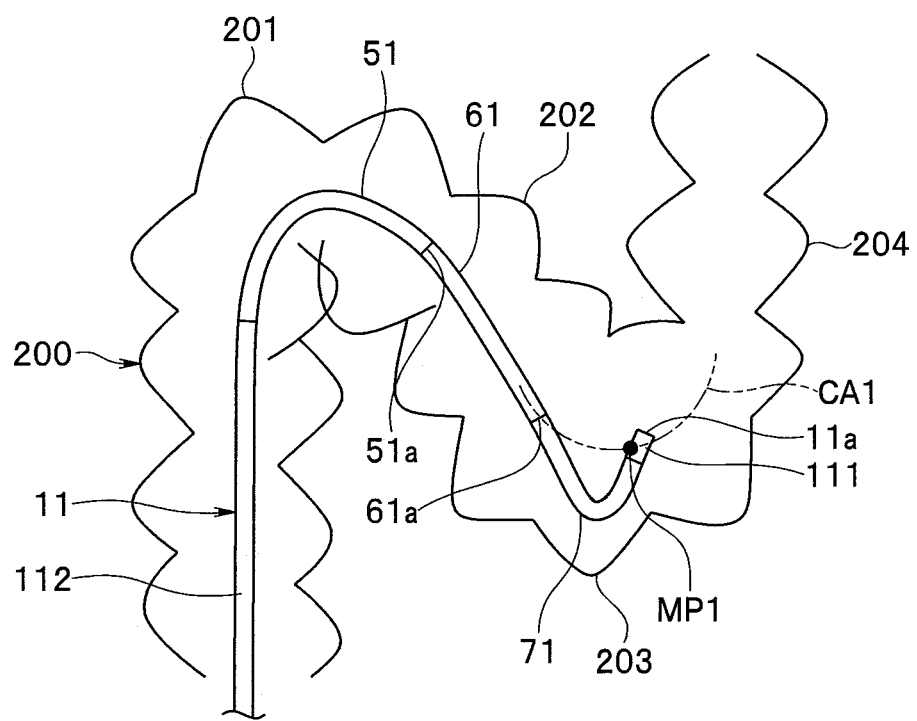
FIG. 9 is an explanatory diagram showing one step in a first example of a propulsion operation for an insertion section in the first embodiment of the present invention.

FIG. 9 is an explanatory diagram showing one step in the first example of the propulsion operation. In the first example, a surgeon inserts the insertion section 11 into a large intestine 200 from an anus of the subject and advances the distal end 11a of the insertion section 11 to a portion near a curve part 203 formed in a combining part of a sigmoid colon 202 and a descending colon 204. At this time, the first tubular section 51 of the first active bending section 5, the second tubular section 61 of the second active bending section 6, and the third tubular section 71 of the third active bending section 7 and the flexible tube section 112 are respectively bent according to a shape of the large intestine 200. The first to third tubular sections 51, 61, and 71 respectively bend with operation by the surgeon or automatically.

As shown in FIG. 9, a center axis CA1 of the curve part 203 and a center point MP1 located in a center in the longitudinal direction in the center axis CA1 are assumed. As shown in FIG. 9, the surgeon advances the distal end 11a of the insertion section 11 to a position further on a depth side of the large intestine 200 than the center point MP1.

Note that length of each of the first to third tubular sections 51, 61, and 71 is preferably length at which, in a state shown in FIG. 9, the first tubular section 51 is located in front of or behind a sigmoid colon top part 201 and the entire second tubular section 61 is located between the sigmoid colon top part 201 and the curve part 203. In the following explanation, it is assumed that the length of each of the first to third tubular sections 51, 61, and 71 is set to the preferred length.

Figure 10:
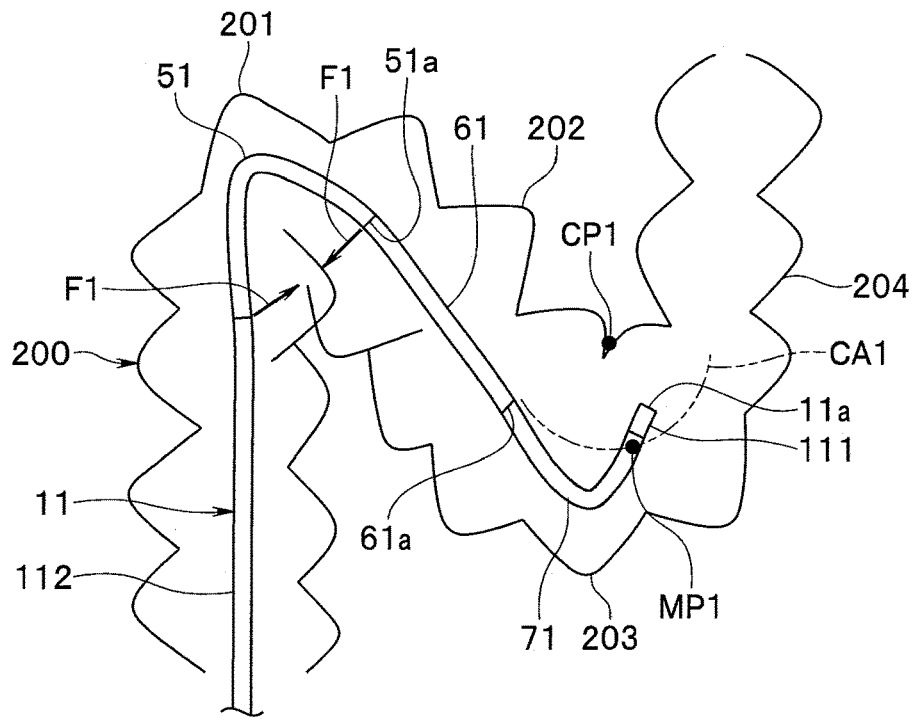

FIG. 10 shows a next step. In this step, the position-information acquiring section 21 (see FIG. 2) acquires first position information, which is information having a correspondence relation with a position of the distal end 11a of the insertion section 11 with respect to the curve part 203, and second position information, which is information having a corresponding relation with a position of the second end portion 61a of the second tubular section 61 with respect to the curve part 203.

In the present embodiment, the first position information is the present position of the distal end 11a of the insertion section 11 determined by the distal-end-position determining section 25 (see FIG. 7). The distal-end-position determining section 25 determines, based on a history of changes of an image recorded in the recording section 24, whether the distal end 11a of the insertion section 11 is located further on the depth side of the large intestine 200 than the center point MP1.

The second position information is the position of the second end portion 61a of the second tubular section 61 determined by the bending-section-position determining section 27 (see FIG. 7). In the present embodiment, the position of the second end portion 61a of the second tubular section 61 is determined based on the curvature of the second tubular section 61. More specifically, for example, when the curvature of the second tubular section 61 is equal to or smaller than a predetermined threshold, that is, a shape of the second tubular section 61 is a shape close to a straight line, the bending-section-position determining section 27 determines that the second end portion 61a of the second tubular section 61 is located further on the anus side than the center point MP1.

In a state shown in FIG. 10, the position-information acquiring section 21 acquires first position information indicating that the distal end 11a of the insertion section 11 is located further on the depth side of the large intestine 200 than the center point MP1 and second position information indicating that the second end portion 61a of the second tubular section 61 is located further on the anus side than the center point MP1.

As shown in FIG. 10, a center point CP1 of an imaginary circle including an arc obtained by approximating the center axis CA1 of the curve part 203 or an imaginary ellipse including an elliptical arc obtained by approximating the center axis CA1 is assumed. When the position-information acquiring section 21 acquires the first position information and the second position information, the first control section 231 of the propulsion control section 23 controls the first driving section 52 such that a first bending operation in which the first end portion 51a of the first tubular section 51 moves away from the center point CP1 is executed (see FIG. 4). In FIG. 10, arrows with a sign F1 indicate a force acting on both ends in the longitudinal direction of the first tubular section 51 in the first bending operation. As is understood from FIG. 9 and FIG. 10, the first tubular section 51 bends with the force F1.

The first tubular section 51 supports a part of the large intestine 200 by bending. In an example shown in FIG. 10, the first tubular section 51 supports the sigmoid colon top part 201. Note that the part of the large intestine 200 supported by the first tubular section 51 is not limited to the sigmoid colon top part 201. A bending amount of the first tubular section 51 is preferably magnitude that does not apply a large load to the large intestine 200. The first tubular section 51 bends, whereby a space for the second tubular section 61 to bend in a second bending operation explained below is secured.

Figure 11:
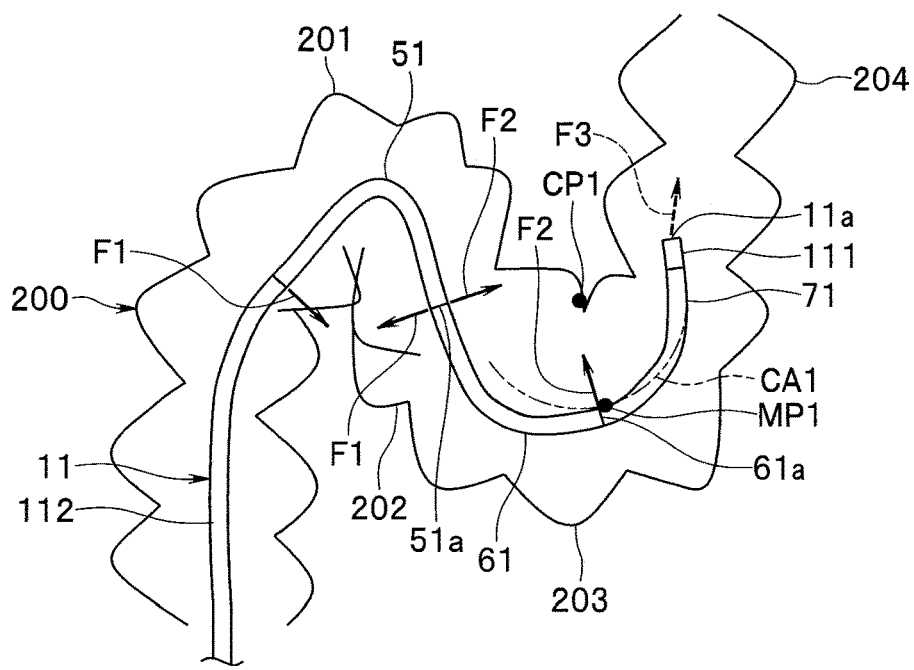
FIG. 11 is an explanatory diagram showing a step following the step shown in FIG. 10.

FIG. 11 shows a next step. In this step, the second control section 232 of the propulsion control section 23 controls the second driving section 62 such that, after the execution of the first bending operation, a second bending operation in which the second end portion 61a of the second tubular section 61 approaches the center point CP1 is executed (see FIG. 4). The third control section 233 of the propulsion control section 23 controls the first driving section 52 such that, during the execution of the second bending operation, operation in which a force in a direction of bending the first tubular section 51 in the first bending operation acts on the first end portion 51a of the first tubular section 51 (hereinafter referred to as supporting operation) is executed (see FIG. 4). In FIG. 11, arrows with the sign F1 indicate the force acting on both the ends in the longitudinal direction of the first tubular section 51 and arrows with a sign F2 indicate the force acting on both ends in the longitudinal direction of the second tubular section 61.

In a state shown in FIG. 11, a state in which the first tubular section 51 supports a part of the large intestine 200 is maintained. In this state, the second tubular section 61 bends, whereby the second end portion 61a of the second tubular section 61 advances to the depth side of the large intestine 200 beyond the center point MP1. As a result, the distal end 11a of the insertion section 11 advances to the depth side of the large intestine 200. In FIG. 11, an arrow with a sign F3 indicates the force acting on the distal end 11a of the insertion section 11 when the second tubular section 61 bends.

Figure 12:
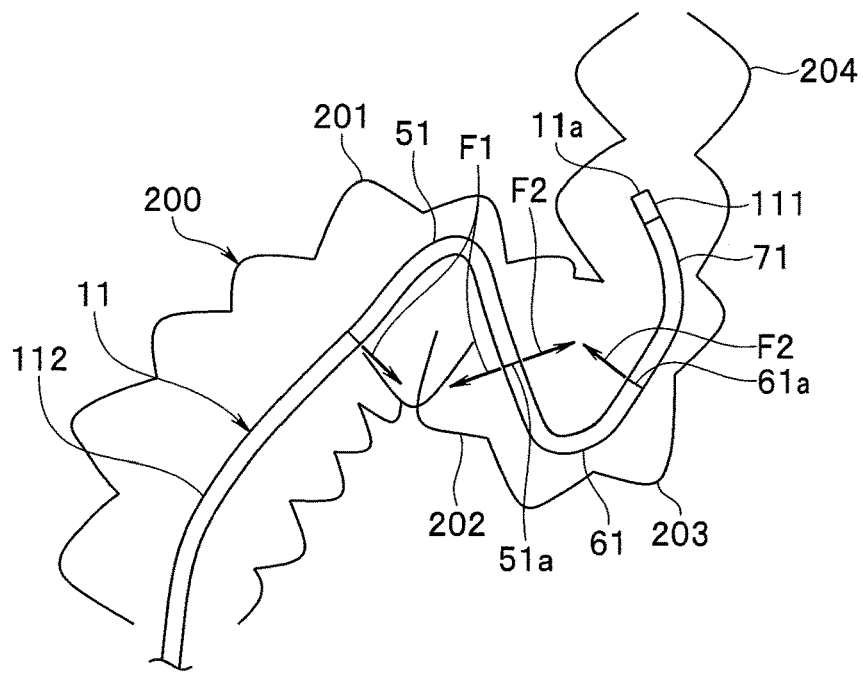
FIG. 12 is an explanatory diagram showing a step following the step shown in FIG. 11.

FIG. 12 shows a next step. In this step, the bending amount of the second tubular section 61 is further increased from the step shown in FIG. 11. Consequently, the distal end 11a of the insertion section 11 further advances to the depth side of the large intestine 200. Note that, in order to prevent a large load from being applied to the large intestine 200, the second control section 232 controls the second driving section 62 such that magnitude of the force caused to act on the second tubular section 61 by the second driving section 62 is reduced to a predetermined threshold or less. The magnitude of the force acting on the second tubular section 61 is controlled according to, for example, magnitude of the force for towing the plurality of wires 62A.

The step shown in FIG. 12 is completed, whereby the propulsion operation for the insertion section 11 is completed. After the completion of the propulsion operation for the insertion section 11, the surgeon pushes in the insertion section 11 and advances the distal end 11a of the insertion section 11 to the depth side of the large intestine 200.

(Second Example of the Propulsion Operation)

Subsequently, a second example of the propulsion operation for the insertion section 11 is explained with reference to FIG. 13 to FIG. 16. The second example is an example in which the distal end 11a of the insertion section 11 is propelled in a portion near a curve part formed in a transverse colon.

Figure 13:
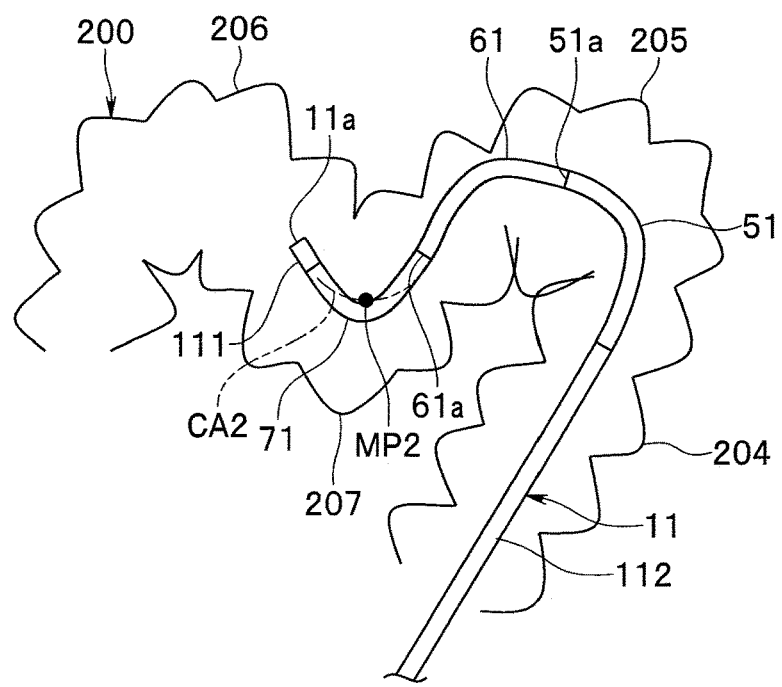
FIG. 13 is an explanatory diagram showing one step in a second example of the propulsion operation for the insertion section in the first embodiment of the present invention.

FIG. 13 is an explanatory diagram showing one step in the second example of the propulsion operation. In the second example, the surgeon advances the distal end 11a of the insertion section 11 to a portion near a curve part 207 formed in a transverse colon 206. At this time, the first tubular section 51 of the first active bending section 5, the second tubular section 61 of the second active bending section 6, and the third tubular section 71 of the third active bending section 7 and the flexible tube section 112 are respectively bent according to the shape of the large intestine 200. The first to third tubular sections 51, 61, and 71 respectively bend with operation by the surgeon or automatically.

As shown in FIG. 13, a center axis CA2 of the curve part 207 and a center point MP2 located in the center in the longitudinal direction in the center axis CA2 are assumed. In the step FIG. 13, the surgeon advances the distal end 11a of the insertion section 11 to a position further on the depth side of the large intestine 200 than the center point MP2.

Note that length of each of the first to third tubular sections 51, 61, and 71 is preferably length at which, in a state shown in FIG. 13, the first tubular section 51 is located in front of or behind a combining part 205 of the descending colon 204 and the transverse colon 206 and the entire second tubular section 61 is located between the combining part 205 and the curve part 207. In the following explanation, it is assumed that the length of each of the first to third tubular sections 51, 61, and 71 is set to the preferred length. Note that the first to third tubular sections 51, 61, and 71 may simultaneously satisfy a requirement of the preferred length and a requirement of the preferred length explained with reference to FIG. 9.

Figure 14:
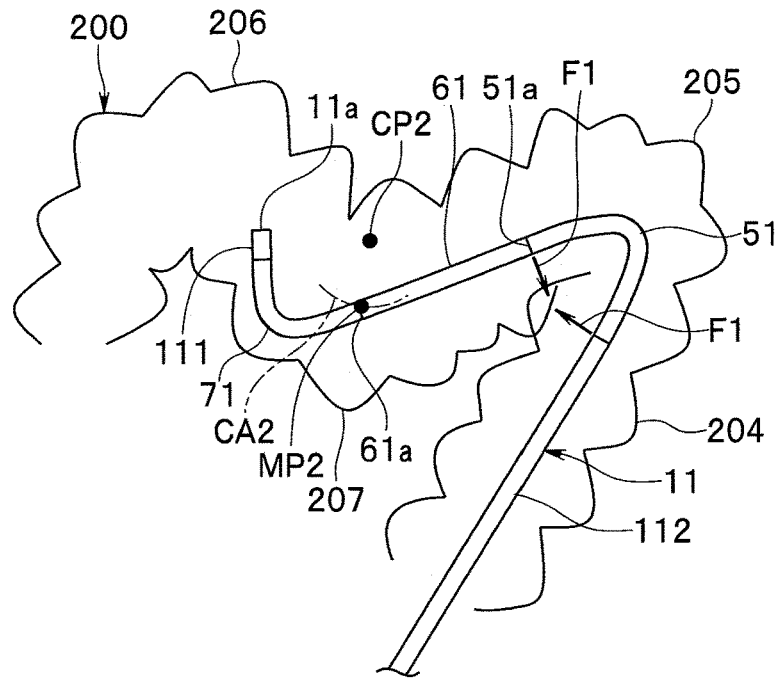
FIG. 14 is an explanatory diagram showing a step following the step shown in FIG. 13.

FIG. 14 shows a next step. In this step, first, as in the step shown in FIG. 10 in the first example, the position-information acquiring section 21 (see FIG. 2) acquires first position information and second position information. Note that, as in the first example, the position of the second end portion 61a of the second tubular section 61 is determined based on the curvature of the second tubular section 61. More specifically, for example, when the curvature of the second tubular section 61 is equal to or smaller than the predetermined threshold, the bending-section-position determining section 27 determines that the second end portion 61a of the second tubular section 61 is located further on the anus side than the center point MP2.

In a state shown in FIG. 14, the position-information acquiring section 21 acquires first position information indicating that the distal end 11a of the insertion section 11 is located further on the depth side of the large intestine 200 than the center point MP2 and second position information indicating that the second end portion 61a of the second tubular section 61 is located further on the anus side than the center point MP2.

As shown in FIG. 14, a center point CP2 of an imaginary circle including an arc obtained by approximating the center axis CA2 of the curve part 207 or an imaginary ellipse including an elliptical arc obtained by approximating the center axis CA2 is assumed. When the position-information acquiring section 21 acquires the first position information and the second position information, the first control section 231 of the propulsion control section 23 controls the first driving section 52 such that a first bending operation in which the first end portion 51a of the first tubular section 51 moves away from the center point CP2 is executed (see FIG. 4). In FIG. 14, arrows with the sign F1 indicate the force acting on both the ends in the longitudinal direction of the first tubular section 51 in the first bending operation.

The first tubular section 51 supports a part of the large intestine 200 by bending. In an example shown in FIG. 14, the first tubular section 51 supports the combining part 205. The first tubular section 51 bends, whereby a space for the second tubular section 61 to bend in a second bending operation explained below is secured.

Figure 15:
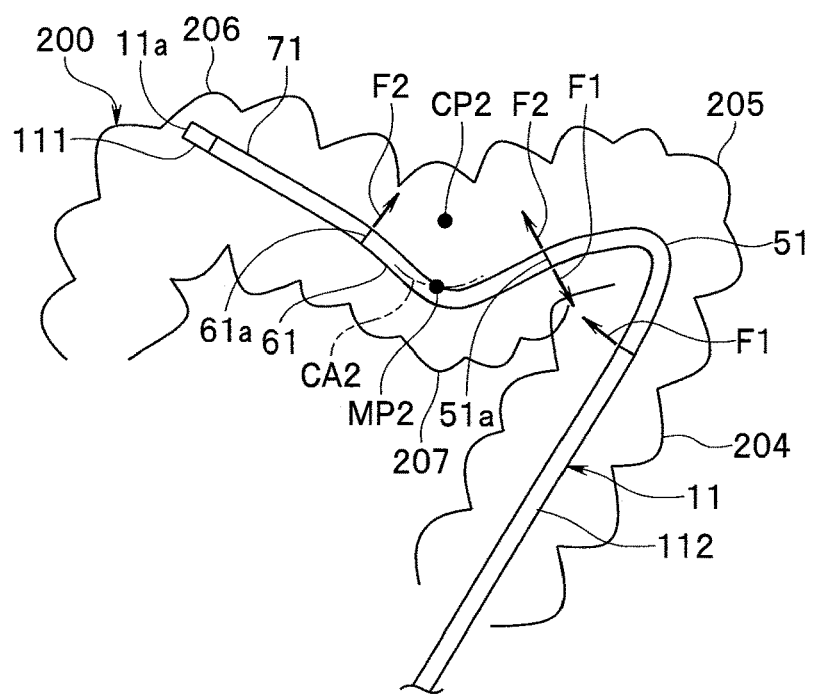
FIG. 15 is an explanatory diagram showing a step following the step shown in FIG. 14.

FIG. 15 shows a next step. In this step, the second control section 232 of the propulsion control section 23 controls the second driving section 62 such that, after the execution of the first bending operation, a second bending operation in which the second end portion 61a of the second tubular section 61 approaches the center point CP2 is executed (see FIG. 4). The third control section 233 of the propulsion control section 23 controls the first driving section 52 such that, during the execution of the second bending operation, a supporting operation in which the force in a direction of bending the first tubular section 51 in the first bending operation acts on the first end portion 51a of the first tubular section 51 is executed (see FIG. 4). In FIG. 15, arrows with the sign F1 indicate the force acting on both the ends in the longitudinal direction of the first tubular section 51 and arrows with the sign F2 indicate the force acting on both the ends in the longitudinal direction of the second tubular section 61.

In a state shown in FIG. 15, a state in which the first tubular section 51 supports a part of the large intestine 200 is maintained. In this state, the second tubular section 61 bends, whereby the second end portion 61a of the second tubular section 61 advances to the depth side of the large intestine 200 beyond the center point MP2. As a result, the distal end 11a of the insertion section 11 advances to the depth side of the large intestine 200.

Note that, in the second example, operation for bending the third tubular section 71 is executed from the step shown in FIG. 15. This operation is explained below.

In the step shown in FIG. 15, the depth-direction-information acquiring section 22 acquires depth direction information indicating a direction of a depth part of the large intestine 200 based on the position of the distal end 11a of the insertion section 11.

Figure 16:
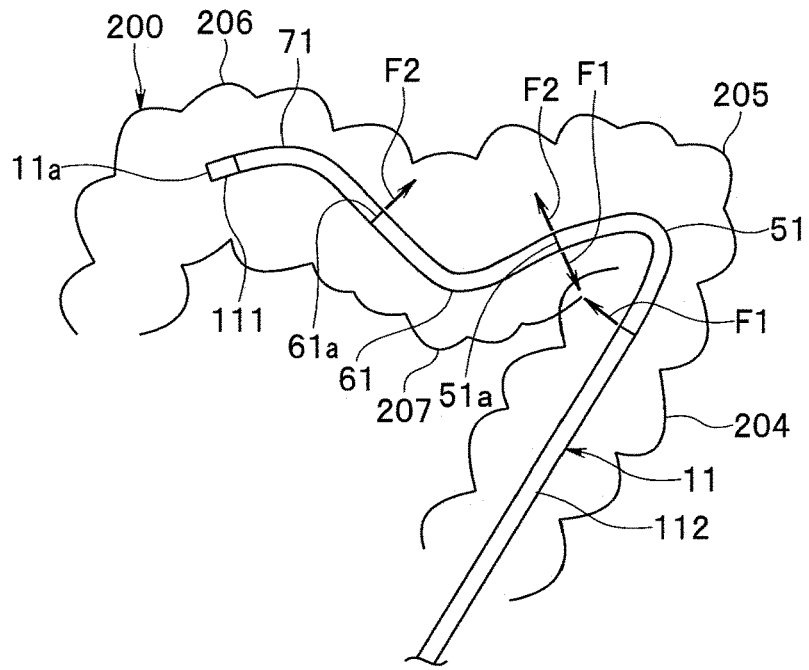
FIG. 16 is an explanatory diagram showing a step following the step shown in FIG. 15.

FIG. 16 shows a next step. In this step, the fourth control section 234 of the propulsion control section 23 controls the third driving section 72 based on the depth direction information such that the distal end 11a of the insertion section 11 faces the depth part of the large intestine 200 (see FIG. 4).

(Propulsion Method for the Insertion Section)

Figure 17:
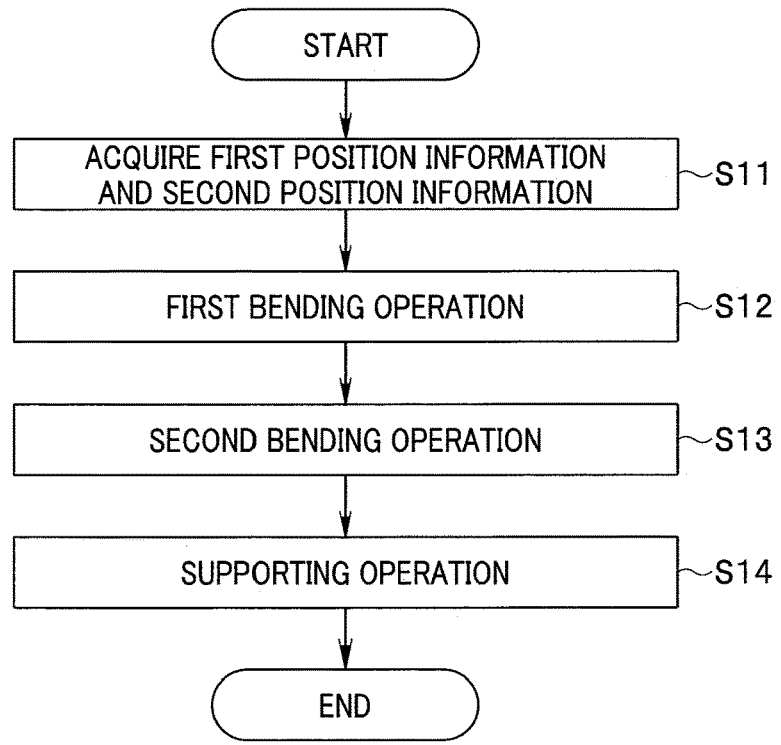
FIG. 17 is a flowchart showing a propulsion method for the insertion section according to the first embodiment of the present invention.

Subsequently, a propulsion method for the insertion section according to the present embodiment is briefly explained with reference to FIG. 17. FIG. 17 is a flowchart showing the propulsion method for the insertion section according to the present embodiment. The propulsion method for the insertion section according to the present embodiment includes steps S11, S12, S13, and S14 shown in FIG. 17.

In step S11, the position-information acquiring section 21 acquires first position information, which is information having a correspondence relation with a position of the distal end 11a of the insertion section 11 with respect to a predetermined curve part (the curve part 203 or 207) in a lumen (the large intestine 200) of a subject, and second position information, which is information having a correspondence relation with a position of the second end portion 61a of the second tubular section 61 with respect to the curve part.

Step S12 is executed when, in step S11, the position-information acquiring section 21 acquires first position information indicating that the distal end 11a of the insertion section 11 is located further on a depth side of the lumen than a center point (the center point MP1 or MP2) located in a center in the longitudinal direction in a center axis of the curve part and second position information indicating that the second end portion 61a of the second tubular section 61 is located further on an inlet side (an anus side) of the lumen than the center point. In step S12, the first control section 231 of the propulsion control section 23 controls the first driving section 52 such that a first bending operation in which the first end portion 51a of the first tubular section 51 moves away from a center point (the center point CP1 or CP2) of an imaginary circle including an arc obtained by approximating the center axis or an imaginary ellipse including an elliptical arc obtained by approximating the center axis is executed.

Step S13 is executed after the execution of the first bending operation in step S12. In step S13, the second control section 232 of the propulsion control section 23 controls the second driving section 62 such that a second bending operation in which the second end portion 61a of the second tubular section 61 approaches the center point is executed.

Step S14 is executed during the execution of the second bending operation in step S13. In step S14, the third control section 233 of the propulsion control section 23 controls the first driving section 52 such that a supporting operation in which the force in a direction of bending the first tubular section 51 in the first bending operation acts on the first end portion 51a of the first tubular section 51 is executed.

(Action and Effects)

Subsequently, action and effects of the endoscope system 100 and the propulsion method for the insertion section according to the present embodiment are explained. In the present embodiment, the distal end 11a of the insertion section 11 can be propelled toward the depth of the lumen by controlling the shapes of the first tubular section 51 and the second tubular section 61 with the first to third control sections 231 to 233 of the propulsion control section 23. In the present embodiment, in order to propel the distal end 11a of the insertion section 11, it is unnecessary to provide a balloon and an extending and contracting mechanism as in the endoscope apparatus disclosed in Japanese Patent Application Laid-Open Publication No. 2009-195321. Consequently, according to the present embodiment, it is possible to propel the distal end 11a of the insertion section 11 toward the depth of the lumen with a simple configuration.

In the present embodiment, the position-information acquiring section 21 acquires information indicating whether the distal end 11a of the insertion section 11 is located further on the depth side of the lumen than the center point (MP1 or MP2) located in the center in the longitudinal direction in the center axis of the predetermined curve part (the curve part 203 or 207) in the lumen (the large intestine 200) of the subject and the second end portion 61a of the second tubular section 61 is located further on the inlet side of the lumen than the center point, the information being information for determining whether to execute the first bending operation (hereinafter referred to as executability determination information). In the present embodiment, it is determined by the distal-end-position determining section 25 (see FIG. 7) whether the distal end 11a of the insertion section 11 is located further on the depth side of the lumen than the center point. In the present embodiment, it is determined, based on the curvature of the second tubular section 61, whether the second end portion 61a of the second tubular section 61 is located further on the inlet side of the lumen than the center point. The curvature of the second tubular section 61 is calculated based on the towing amount of each of the plurality of wires 62A detected by the towing-amount detecting section 26A. According to the present embodiment, compared with a case in which a sensor that detects an insertion shape of the insertion section 11 and a position of the distal end 11a of the insertion section 11 is used, it is possible to easily acquire the executability determination information.

Note that, in the present embodiment, the position-information acquiring section 21 acquires the executability determination information by acquiring the first position information, which is the information having the correspondence relation with the position of the distal end 11a of the insertion section 11, and the second position information having the correspondence relation with the position of the second end portion 61a of the second tubular section 61. In the present embodiment, in particular, the first position information indicates the position itself of the distal end 11a of the insertion section 11. However, an acquiring method for the executability determination information is not limited to the example explained above. For example, the first position information may be information concerning a position a predetermined distance away from the distal end 11a of the insertion section 11. Alternatively, the position indicated by the first position information and the position indicated by the second position information may be the same position. In this case, the position-information acquiring section 21 substantially acquires information concerning a position of any one point of the insertion section 11 to thereby acquire the executability determination information indicating whether the distal end 11a of the insertion section 11 is located further on the depth side of the lumen than the center point and the second end portion 61a of the second tubular section 61 is located further on the inlet side of the lumen than the center point. The position of the any one point may be, for example, a position a predetermined distance away from the second end portion 61a of the second tubular section 61 toward the distal end 11a of the insertion section 11.

In the present embodiment, as explained in the second example, the third driving section 72 is controlled based on the depth direction information acquired by the depth-direction-information acquiring section 22 to bend the third tubular section 71 such that the distal end 11a of the insertion section 11 faces the depth of the lumen. However, not only in the second example but also in the first example, the third driving section 72 may be controlled to bend the third tubular section 71.

Note that the third active bending section 7 and the depth-direction-information acquiring section 22 are not essential components of the endoscope system 100 according to the present embodiment and may not be provided. In this case, a bending section may be provided between the distal end portion 111 in the insertion section 11 and the second tubular section 61. The bending section is configured to be bent in upper, lower, left, and right four directions by, for example, two bending operation knobs (not illustrated) provided in the operation section 12 (see FIG. 1) of the endoscope 1.

(Modification)

Figure 18:
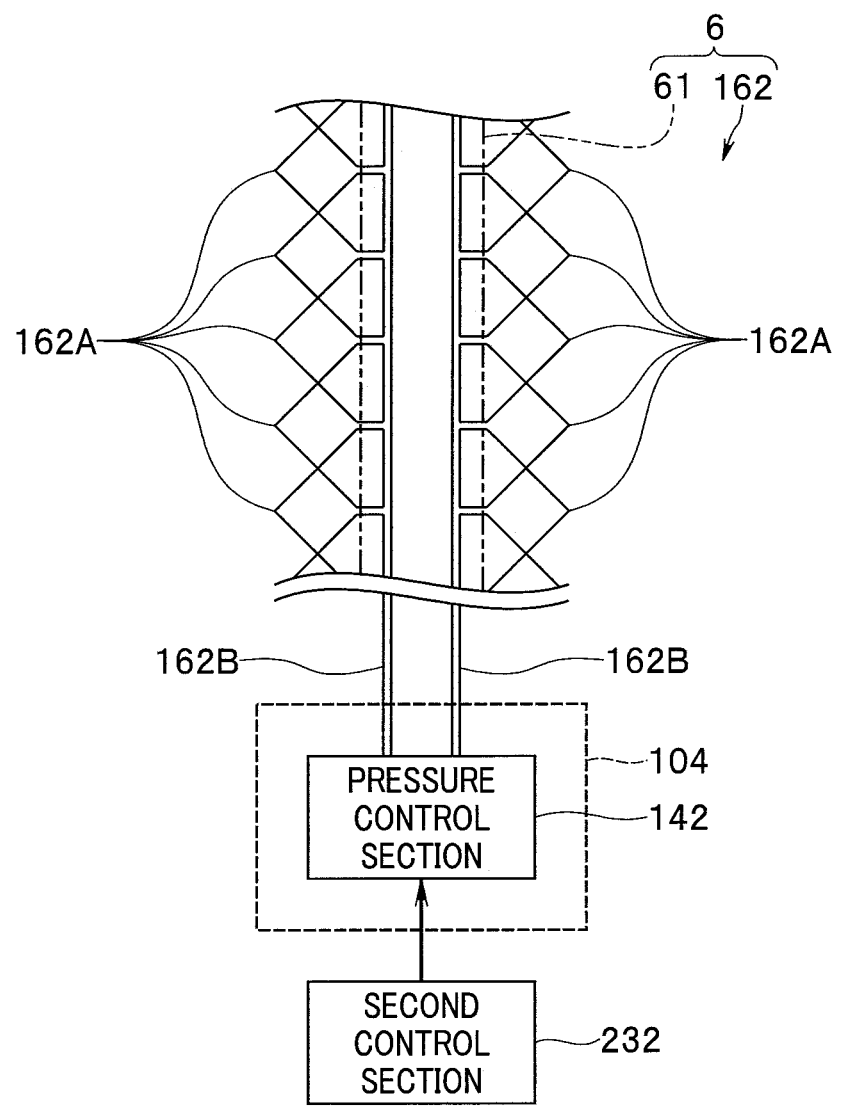
FIG. 18 is an explanatory diagram showing a configuration of a modification of the second active bending section in the first embodiment of the present invention.

Subsequently, a modification of the first to third active bending sections 5 to 7 in the present embodiment is explained. In the modification, a configuration of the driving sections of the first to third active bending sections 5 to 7 is different. The second active bending section 6 is explained as an example. FIG. 18 is an explanatory diagram showing a configuration of a modification of the second active bending section 6.

In the modification, the second active bending section 6 includes, instead of the second driving section 62, a second driving section 162 that bends the second tubular section 61.

The second driving section 162 includes a plurality of pressure chambers 162A provided in an outer circumferential portion of the second tubular section 61. The plurality of pressure chambers 162A are arranged side by side in the longitudinal direction of the second tubular section 61 and arranged side by side in two or more rows (for example, four rows) in positions different from one another in an axial direction of the second tubular section 61. The plurality of pressure chambers 162A respectively expand and contract according to pressures applied to the pressure chambers 162A.

The second driving section 162 includes, besides the plurality of pressure chambers 162A, a plurality of fluid supply conduits 162B provided in the second tubular section 61. The fluid supply conduit 162B is a conduit for supplying fluid for controlling pressure in each of the plurality of pressure chambers 162A. For example, one fluid supply conduit 162B is used to control the pressure in each of the plurality of pressure chambers 162A arranged in one row in the longitudinal direction of the second tubular section 61 in any position in the axial direction of the second tubular section 61.

In the modification, a pressure control apparatus 104 is provided instead of the towing apparatus 4. The second driving section 162 further includes a pressure control section 142 provided in the pressure control apparatus 104. The pressure control section 142 is configured to be able to control a flow rate and pressure of the fluid supplied to each of the plurality of fluid supply conduits 162B.

Figure 19:
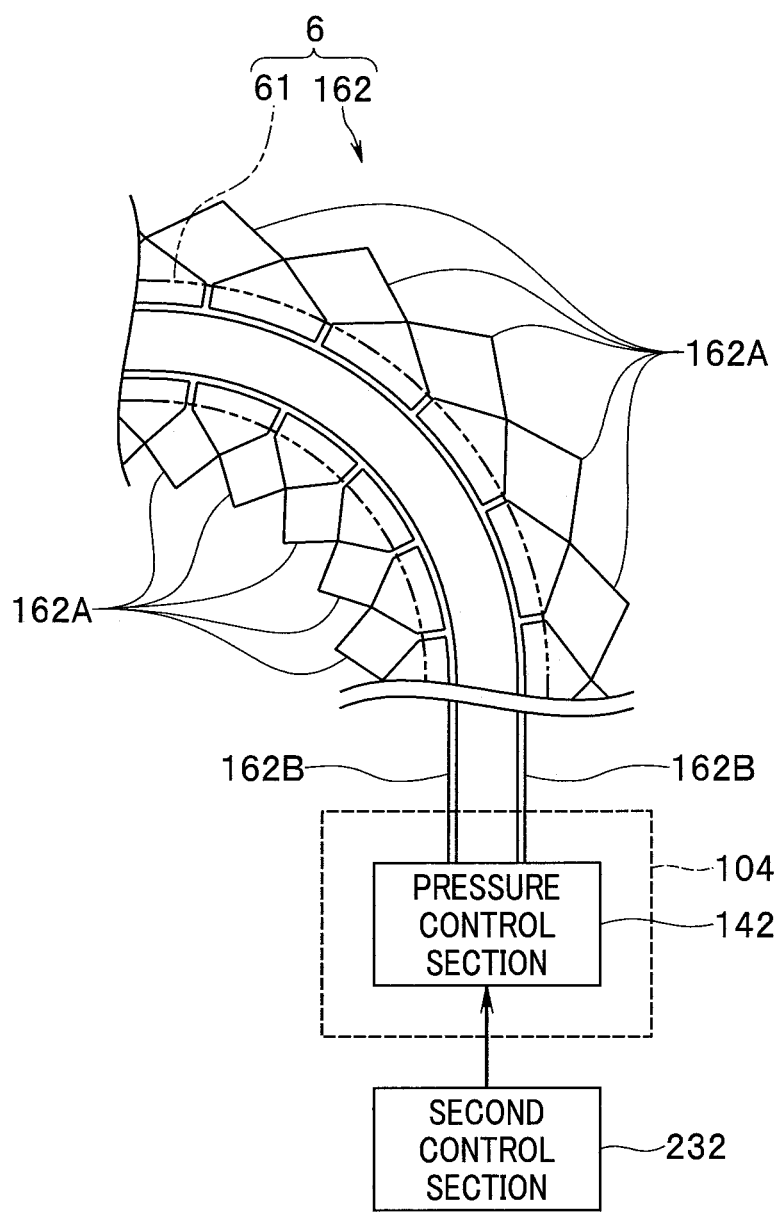
FIG. 19 is an explanatory diagram for explaining operation of the modification of the second active bending section in the first embodiment of the present invention.

Subsequently, operation of the second driving section 162 is explained with reference to FIG. 19. In the present embodiment, the pressure control section 142 of the second driving section 162 bends the second tubular section 61 by controlling the flow rate and the pressure of the fluid supplied to each of the plurality of fluid supply conduits 162B to control the pressure in each of the plurality of pressure chambers 162A. In FIG. 19, an example is shown in which the plurality of pressure chambers 162A are contracted by reducing pressures in the plurality of pressure chambers 162A arranged in one row on a left side in FIG. 19 and the plurality of pressure chambers 162A are expanded by increasing pressures in the plurality of pressure chambers 162A arranged in one row on a right side in FIG. 19 to bend the second tubular section 61. A direction and a size of the bending of the second tubular section 61 can be controlled according to magnitude of the pressure in each of the plurality of pressure chambers 162A. Note that the pressure control section 142 is controlled by the second control section 232 of the propulsion control section 23.

The second active bending section 6 is explained as an example above. A configuration and operation of the driving sections of the first and third active bending sections 5 and 7 are the same as the configuration and the operation of the second driving section 162. In other words, the first active bending section 5 includes, instead of the first driving section 52, a first driving section that bends the first tubular section 51. The first driving section includes a plurality of pressure chambers provided in an outer circumferential portion of the first tubular section 51, a plurality of fluid supply conduits provided in the first tubular section 51, and a pressure control section provided in the pressure control apparatus 104. In the modification, the pressure control section of the first driving section bends the first tubular section 51 by controlling a flow rate and pressure of fluid supplied to each of the plurality of fluid supply conduits to control pressure in each of the plurality of pressure chambers.

The third active bending section 7 includes, instead of the third driving section 72, a third driving section that bends the third tubular section 71. The third driving section includes a plurality of pressure chambers provided in an outer circumferential portion of the third tubular section 71, a plurality of fluid supply conduits provided in the third tubular section 71, and a pressure control section provided in the pressure control apparatus 104. In the modification, the pressure control section of the third driving section bends the third tubular section 71 by controlling a flow rate and pressure of fluid supplied to each of the plurality of fluid supply conduits to control pressure in each of the plurality of pressure chambers.

Second Embodiment

Figure 20:
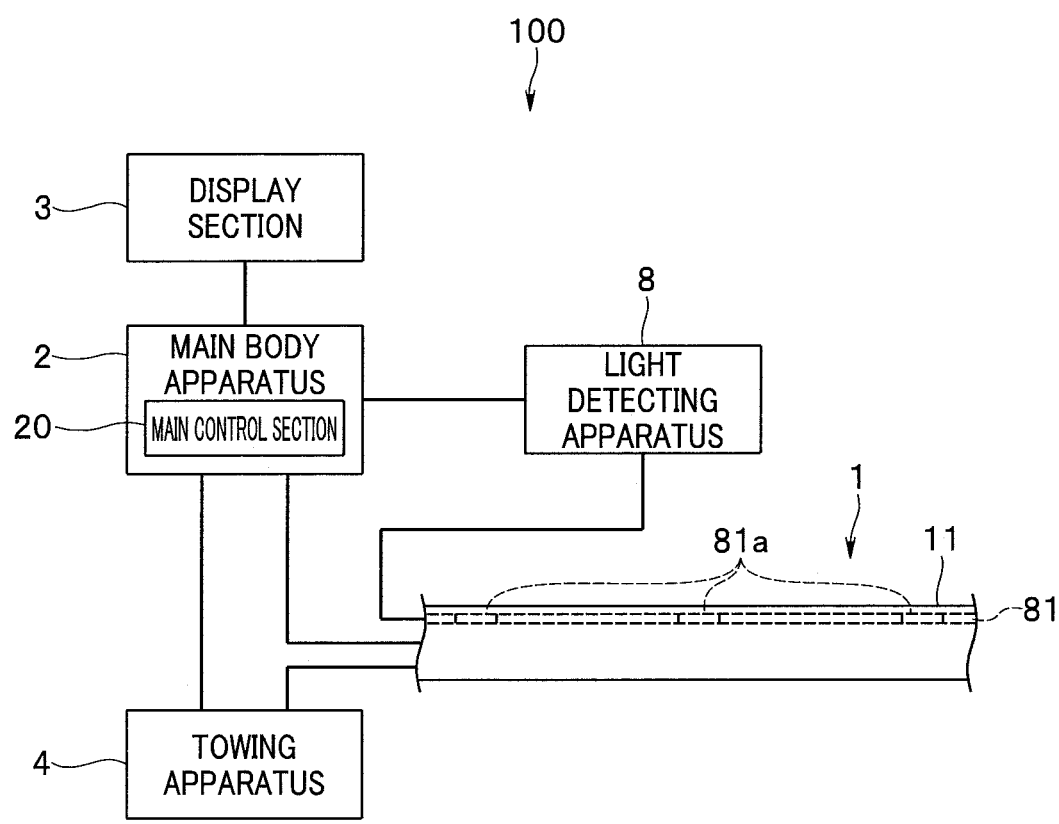
FIG. 20 is an explanatory diagram showing a schematic configuration of an endoscope system according to a second embodiment of the present invention.
Figure 21:
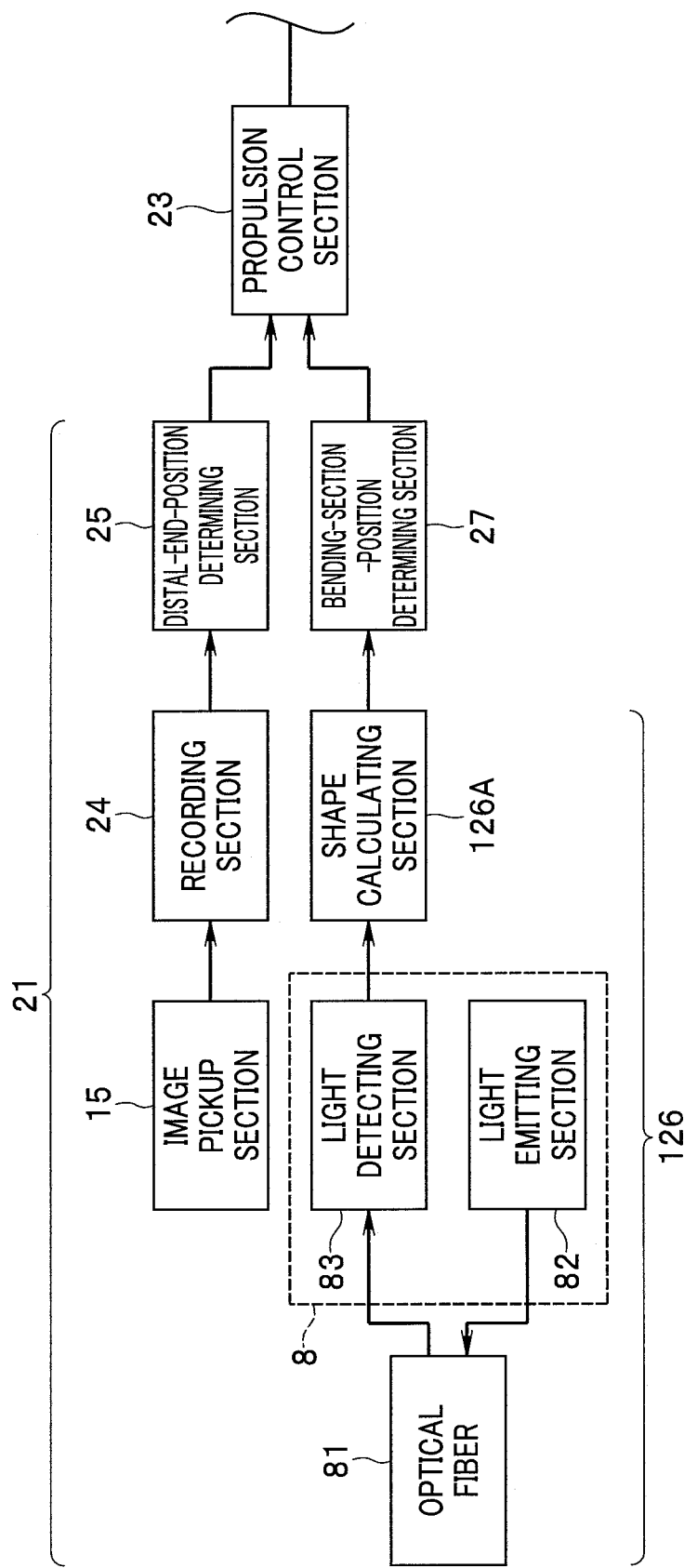
FIG. 21 is a functional block diagram showing a configuration of a position-information acquiring section in the second embodiment of the present invention.

Subsequently, an endoscope system according to a second embodiment of the present invention is explained with reference to FIG. 20 and FIG. 21. FIG. 20 is an explanatory diagram showing a schematic configuration of the endoscope system according to the present embodiment. FIG. 21 is a functional block diagram showing a configuration of a position-information acquiring section in the present embodiment.

In the present embodiment, a configuration of the position-information acquiring section 21 is different from the configuration in the first embodiment. In other words, in the present embodiment, the position-information acquiring section 21 includes, instead of the shape sensor 26 in the first embodiment, a shape sensor 126 that detects a shape of the second tubular section 61 of the second active bending section 6. The shape sensor 126 is an optical fiber sensor and includes an optical fiber 81 provided in the insertion section 11 of the endoscope 1.

In the present embodiment, the endoscope system 100 includes a light detecting apparatus 8 connected to the main body apparatus 2. The shape sensor 126 further includes a light emitting section 82 and a light detecting section 83 provided in the light detecting apparatus 8. The light emitting section 82 emits detection light made incident on the optical fiber 81. The light detecting section 83 detects the detection light transmitted through the optical fiber 81.

The shape sensor 126 further includes a shape calculating section 126A provided in the main body apparatus 2. The shape calculating section 126A calculates a shape of the second tubular section 61, that is, a direction and a size of bending of the second tubular section 61 and calculates a curvature of the second tubular section 61, based on a detection result of the light detecting section 83.

A calculating method for a shape of the second tubular section 61 by the shape sensor 126 is more specifically explained below. The optical fiber 81 includes a plurality of portions to be detected 81a disposed at a predetermined interval in the longitudinal direction. The portions to be detected 81a are portions applied with working for leaking or absorbing light having a light amount corresponding to a bending amount of the optical fiber 81 to an outside of the optical fiber 81. The light detecting section 83 detects a bending position and a bending amount of the second tubular section 61 by detecting detection light that changes according to the bending amount of the optical fiber 81.

The shape calculating section 126A calculates a direction and a size of bending of the second tubular section 61 and calculates a curvature of the second tubular section 61, based on the detected bending position and the detected bending amount.

Note that the shape sensor 126 can detect not only the shape of the second tubular section 61 but also a shape of the insertion section 11 other than the second tubular section 61 in which the portions to be detected 81a are disposed.

In an example shown in FIG. 20, the number of optical fibers 81 is one. However, the number of optical fibers 81 may be plural. The plurality of optical fibers 81 are respectively disposed in positions different from one another in the axial direction of the insertion section 11. The plurality of portions to be detected 81a are arranged side by side in the longitudinal direction of the insertion section 11 and arranged side by side in two or more rows (for example, four rows) in positions different from one another in the axial direction of the insertion section 11. A direction and a size of bending of the second tubular section 61 are calculated based on a bending position and a bending amount detected for each of the plurality of optical fibers 81.

The other configurations, action, and effects in the present embodiment are the same as the configurations, the action, and the effects in the first embodiment.

Third Embodiment

Figure 22:
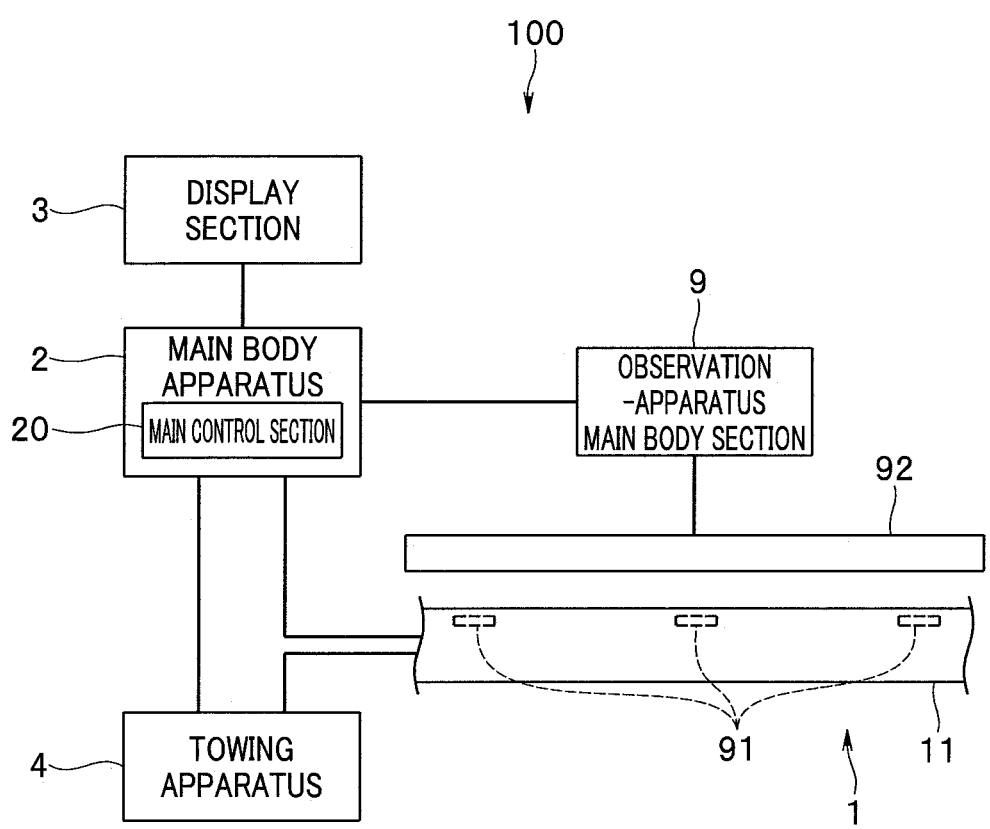
FIG. 22 is an explanatory diagram showing a schematic configuration of an endoscope system according to a third embodiment of the present invention.
Figure 23:
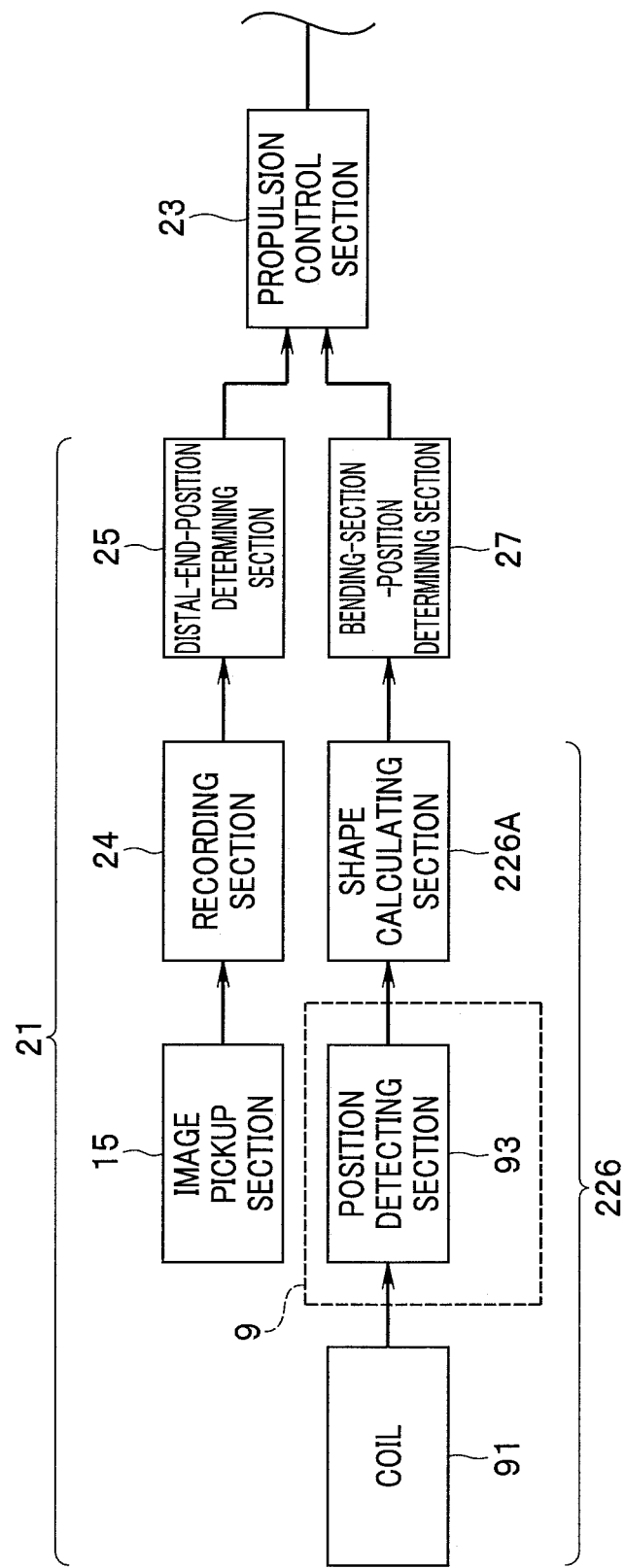
FIG. 23 is a functional block diagram showing a configuration of a position-information acquiring section in the third embodiment of the present invention.

Subsequently, an endoscope system according to a third embodiment of the present invention is explained with reference to FIG. 22 and FIG. 23. FIG. 22 is an explanatory diagram showing a schematic configuration of the endoscope system according to the present embodiment. FIG. 23 is a functional block diagram showing a configuration of a position-information acquiring section in the present embodiment.

In the present embodiment, a configuration of the position-information acquiring section 21 is different from the configuration in the first embodiment. In other words, in the present embodiment, the position-information acquiring section 21 includes, instead of the shape sensor 26 in the first embodiment, a shape sensor 226 that detects a shape of the second tubular section 61 of the second active bending section 6. The shape sensor 226 is an endoscope-insertion-shape observing apparatus that observes an insertion state of the insertion section 11. The shape sensor 226 includes a plurality of coils 91 provided in the insertion section 11 of the endoscope 1. The plurality of coils 91 are arranged side by side in the longitudinal direction of the insertion section 11.

In the present embodiment, the endoscope system 100 includes an observation-apparatus main body section 9 connected to the main body apparatus 2 and a reception antenna 92 connected to the observation-apparatus main body section 9. The plurality of coils 91 respectively generate magnetic fields by being controlled by a not-shown control section provided in the observation-apparatus main body section 9. The shape sensor 126 further includes a position detecting section 93 provided in the observation-apparatus main body section 9. The position detecting section 93 detects a position of each of the plurality of coils 91 by detecting, via the reception antenna 92, a plurality of magnetic fields generated by each of the plurality of coils 91.

The shape sensor 226 further includes a shape calculating section 226A provided in the main body apparatus 2. The shape calculating section 226A calculates a shape of the second tubular section 61, that is, a direction and a size of bending of the second tubular section 61 and calculates a curvature of the second tubular section 61, based on the position of each of the plurality of coils 91 detected by the position detecting section 93.

Note that the shape sensor 226 can detect not only the shape of the second tubular section 61 but also a shape of the insertion section 11 other than the second tubular section 61 in which the coils 91 are disposed.

The other configurations, action, and effects in the present embodiment are the same as the configurations, the action, and the effects in the first embodiment.

The present invention is not limited to the embodiments explained above. Various changes, alterations, and the like are possible in a range in which the gist of the present invention is not changed. For example, the position-information acquiring section 21 may acquire the first position information, which is the information having the correspondence relation with the position of the distal end 11a of the insertion section 11, by detecting pressure acting on the insertion section 11, an insertion length of the insertion section 11, fluoroscopy by an X ray or the like, or a magnetic field generated by a magnet provided at the distal end portion of the insertion section 11.

The position-information acquiring section 21 may acquire, based on a shape of a portion from the distal end 11a of the insertion section 11 to the second tubular section 61, the second position information, which is the information having the correspondence relation with the position of the second end portion 61a of the second tubular section 61.

The endoscope system and the propulsion method for the insertion section of the present invention may be applied to a case in which the insertion section is inserted into not only the intestinal tract of the large intestine but also a digestive tract other than the large intestine, a urinary tract, a blood vessel, and the like.

The endoscope system of the present invention may be an industrial endoscope system. In this case, the endoscope system and the propulsion method for the insertion section of the present invention may be applied to a case in which the insertion section is inserted into a gas pipe, a water pipe, and the like.

What is claimed is:

1. An endoscope system comprising:
    an insertion section extending in a longitudinal direction from a distal end to a proximal end, the insertion section being configured to be inserted distally into a lumen of a subject from an inlet of the lumen, the insertion section comprising:
        a first active bending section including a first tubular section having flexibility, the first active bending section having a first distal end portion;
        a second active bending section provided distally relative to the first tubular section, the second active bending section including a second tubular section having flexibility, the second tubular section having a second distal end portion;
    a first driving section including a first motor configured to bend the first tubular section;
    a second driving section including a second motor configured to bend the second tubular section; and
    a processor comprising hardware, the processor is configured to determine whether the distal end of the insertion section is located deeper into the lumen than a center of a predetermined curve in a center axis direction of the lumen, and
    when the distal end is determined to be located deeper than the center, the processor is configured to:
        control the first driving section to move the first distal end portion in a first direction away from a radial center point of the predetermined curve,
        subsequent to controlling the first driving section, control the second driving section to move the second distal end portion toward the radial center point, and
        concurrently with the controlling of the second driving section, control the first driving section such that a force, in the first direction, acts on the first distal end portion.

2. The endoscope system according to claim 1, wherein the processor is further configured to determine whether the second distal end portion is not located deeper than the center, and
    when the distal end is determined to be located deeper than the center and the second distal end portion is determined not to be located deeper than the center, the processor is configured to control the first driving section to move the first distal end portion in the first direction away from the radial center point of the predetermined curve.

3. The endoscope system according to claim 2, further comprising a shape sensor configured to detect a shape of the second tubular section,
    wherein the determining of whether the second distal end portion is not located deeper than the center is further based on a detection result of the shape sensor.

4. The endoscope system according to claim 3, wherein the second driving section includes a plurality of wires configured to bend the second tubular section and the second motor is configured to tow the plurality of wires, and
    the processor is further configured to detect a towing amount of each of the plurality of wires and calculate the shape of the second tubular section based on the towing amount.

5. The endoscope system according to claim 3, wherein the shape sensor includes an optical fiber provided in the insertion section, a light emitting section that emits detection light made incident on the optical fiber, and a light detecting section that detects the detection light transmitted through the optical fiber, and
    the processor is further configured to calculate the shape of the second tubular section based on a detection result of the light detecting section.

6. The endoscope system according to claim 3, further comprising a reception antenna, wherein
    the shape sensor includes a plurality of coils provided in the insertion section, and
    the processor is further configured to detect a position of each of the plurality of coils by detecting, via the reception coil, a magnetic field generated by each of the plurality of coils and calculate the shape of the second tubular section based on the detected position of each of the plurality of coils.

7. The endoscope system according to claim 3, wherein the determining of whether the second distal end portion is not located deeper than the center is further based on a curvature of the second tubular section.

8. The endoscope system according to claim 1, further comprising:
    an image sensor configured to acquire an image of an object in the lumen; and
    a memory configured to record the image,
    wherein the determining of whether the distal end of the insertion section is located deeper into the lumen than the center is further based on a history of changes of the image recorded in the memory.

9. The endoscope system according to claim 1, further comprising a third active bending section including a third tubular section having flexibility, the third active bending section provided distally relative to the second tubular section; and
 a third driving section including a third motor configured to bend the third tubular section,
 wherein the processor is configured to:
  determine a lumen direction of a portion of the lumen corresponding to the distal end of the insertion section; and
  control the third driving section based on the determined lumen direction to move the distal end of the insertion portion to face the lumen direction.

10. The endoscope system according to claim 9, further comprising an image sensor configured to acquire an image of an object in the lumen,
 wherein the determining of the lumen direction is further based on the image.

11. A propulsion method for an insertion section in an endoscope system,
 the endoscope system comprising:
  an insertion section extending in a longitudinal direction from a distal end to a proximal end, the insertion section being configured to be inserted distally into a lumen of a subject from an inlet of the lumen, the insertion section comprising:
   a first active bending section including a first tubular section having flexibility and the first active bending section having a first distal end portion;
   a second active bending section provided distally relative to the first tubular section, the second active bending section including a second tubular section having flexibility, the second tubular section having a second distal end portion, and
  a processor comprising hardware,
 the propulsion method comprising:
  determining, using the processor, whether the distal end of the insertion section is located deeper into the lumen than a center of a predetermined curve in a center axis direction of the lumen; and
  when the distal end is determined to be located deeper than the center:
   controlling the first active bending section with the processor to move the first distal end portion in a first direction away from a radial center point of the predetermined curve;
   subsequent to moving the first distal end portion, controlling the second active bending section with the processor to move the second distal end portion toward the radial center point; and
   concurrently with the controlling of the second active bending section, applying a force, in the first direction to act on the first distal end portion.

* * * * *